United States Patent
Phukan et al.

(10) Patent No.: US 9,498,409 B2
(45) Date of Patent: *Nov. 22, 2016

(54) COSMETIC SKIN COVERING SHEETS AND THEIR METHOD OF PREPARATION

(71) Applicant: Momentive Performance Materials Inc., Waterford, NY (US)

(72) Inventors: Monjit Phukan, Bangalore (IN); Anubhav Saxena, Bangalore (IN); Mayank Kumar Dubey, Bangalore (IN); Tushar Navale, Mumbai (IN); Richard A. Presti, Airmont, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/572,118

(22) Filed: Dec. 16, 2014

(65) Prior Publication Data

US 2016/0166476 A1  Jun. 16, 2016

(51) Int. Cl.
| | | |
|---|---|---|
| *A61K 8/02* | (2006.01) | |
| *A61Q 19/02* | (2006.01) | |
| *A61Q 19/00* | (2006.01) | |
| *A61Q 17/04* | (2006.01) | |
| *A61K 8/891* | (2006.01) | |

(Continued)

(52) U.S. Cl.
CPC ............. *A61K 8/0208* (2013.01); *A61K 8/891* (2013.01); *A61K 8/895* (2013.01); *A61K 8/899* (2013.01); *A61Q 17/04* (2013.01); *A61Q 19/00* (2013.01); *A61Q 19/02* (2013.01); *A61Q 19/04* (2013.01); *A61Q 19/08* (2013.01); *C08G 77/44* (2013.01); *A61K 2800/56* (2013.01); *A61K 2800/87* (2013.01); *A61K 2800/95* (2013.01)

(58) Field of Classification Search
CPC .... A61K 8/0208; A61K 8/895; A61K 8/891; A61K 8/899; A61K 2800/87; A61K 2800/56; A61K 2800/95; A61Q 19/04; A61Q 19/08; A61Q 19/00; A61Q 17/04; A61Q 19/02; C08G 77/44

See application file for complete search history.

(56) References Cited

U.S. PATENT DOCUMENTS

| | | | |
|---|---|---|---|
| 3,159,601 | A | 12/1964 | Ashby |
| 3,159,662 | A | 12/1964 | Ashby |

(Continued)

FOREIGN PATENT DOCUMENTS

| | | |
|---|---|---|
| JP | 06-247835 A | 2/1993 |
| JP | 06-247827 A | 9/1994 |

(Continued)

OTHER PUBLICATIONS

J.L. Spier, "Homogeneous Catalysis vol. 17, (1979) pp. 407-447, F.G.A. Metals, In Advances in Organometallic Chemistry", vol. 17, (1979) pp. 407-447, F.G.A. Stone & R. West Editors, Academic Press.

(Continued)

*Primary Examiner* — Aradhana Sasan
(74) *Attorney, Agent, or Firm* — Joseph S. Ostroff

(57) ABSTRACT

The invention is directed to a cosmetic skin covering sheet which comprises a patch containing a cosmetic material for application to the skin or a cosmetic formulation which forms the cosmetic skin covering sheet in-situ upon topical application of the cosmetic formulation onto the skin, wherein each of said patch or cosmetic formulation comprises an ionic silicone as described herein.

19 Claims, 1 Drawing Sheet

(51) Int. Cl.
*C08G 77/44* (2006.01)
*A61Q 19/08* (2006.01)
*A61K 8/895* (2006.01)
*A61Q 19/04* (2006.01)
*A61K 8/899* (2006.01)

(56) References Cited

U.S. PATENT DOCUMENTS

| | | | |
|---|---|---|---|
| 3,220,972 | A | 11/1965 | Lamoreaux |
| 3,445,420 | A | 5/1969 | Kookootsedes et al. |
| 3,715,334 | A | 2/1973 | Karstedt |
| 3,775,452 | A | 11/1973 | Karstedt |
| 3,814,730 | A | 6/1974 | Karstedt |
| 4,256,870 | A | 3/1981 | Eckberg |
| 4,279,717 | A | 7/1981 | Eckberg et al. |
| 4,465,818 | A | 8/1984 | Shirahata et al. |
| 4,562,096 | A | 12/1985 | Lo et al. |
| 4,987,169 | A | 1/1991 | Kuwata et al. |
| 5,354,796 | A | 10/1994 | Creecy et al. |
| 5,493,041 | A | 2/1996 | Biggs et al. |
| 5,629,387 | A | 5/1997 | Frances et al. |
| 5,654,362 | A | 8/1997 | Schulz, Jr. et al. |
| 5,663,752 | A | 9/1997 | Imamura et al. |
| 5,760,116 | A | 6/1998 | Kilgour et al. |
| 5,811,487 | A | 9/1998 | Schulz, Jr. et al. |
| 6,124,490 | A | 9/2000 | Gormley et al. |
| 6,296,869 | B1 | 10/2001 | Crotty et al. |
| 6,423,322 | B1 | 7/2002 | Fry |
| 6,531,540 | B1 | 3/2003 | O'Brien |
| 6,761,896 | B1 * | 7/2004 | Znaiden ............... A61K 8/0208 424/401 |
| 7,381,769 | B2 | 6/2008 | O'Brien |
| 7,687,574 | B2 | 3/2010 | Lu et al. |
| 7,700,530 | B2 | 4/2010 | Mundschau et al. |
| 7,833,541 | B2 | 11/2010 | Lu et al. |
| 8,697,829 | B2 | 4/2014 | Saxena et al. |
| 8,703,881 | B2 * | 4/2014 | Saxena ............... A61K 8/896 525/477 |
| 8,722,422 | B2 * | 5/2014 | Briggs ............... F17D 3/00 436/174 |
| 8,772,422 | B2 * | 7/2014 | Saxena ............... C08G 77/38 525/474 |
| 8,835,583 | B2 * | 9/2014 | Saxena ............... C09D 183/08 522/99 |
| 8,974,775 | B2 * | 3/2015 | Saxena ............... A01N 25/10 424/401 |
| 2013/0171080 | A1 * | 7/2013 | Sarkar ............... A61K 8/899 424/59 |
| 2013/0172192 | A1 | 7/2013 | Saxena et al. |
| 2013/0172193 | A1 * | 7/2013 | Saxena ............... A01N 25/10 504/360 |
| 2013/0172419 | A1 | 7/2013 | Saxena et al. |
| 2013/0172427 | A1 | 7/2013 | Saxena et al. |
| 2014/0017188 | A1 * | 1/2014 | Sarkar ............... A61K 8/899 424/64 |

FOREIGN PATENT DOCUMENTS

| | | |
|---|---|---|
| WO | 00/08087 A1 | 2/2000 |
| WO | 2013103535 | 7/2013 |
| WO | 2013103537 | 7/2013 |

OTHER PUBLICATIONS

U.S. Appl. No. 14/572,139 for Applicants Alok Sarkar et al. filed Dec. 16, 2014.
U.S. Appl. No. 14/572,132 for Applicants Anubhav Saxena et al. filed Dec. 16, 2014.
U.S. Appl. No. 14/572,108 for Applicants Monjit Phukan et al. filed Dec. 16, 2014.
Ghanshyam et al., "A Review of Current and Novel Trends for Anti-Aging Formulation", (Apr. 1, 2014), International Journal of Pharmaceutical, Chemical and Biological Sciences, p. 118-1252, Retrieved from the Internet (Feb. 15, 2016): http://www.ijpcbs.com/files/17-421.
International Search Report and Written Opinion dated Mar. 15, 2016.

* cited by examiner

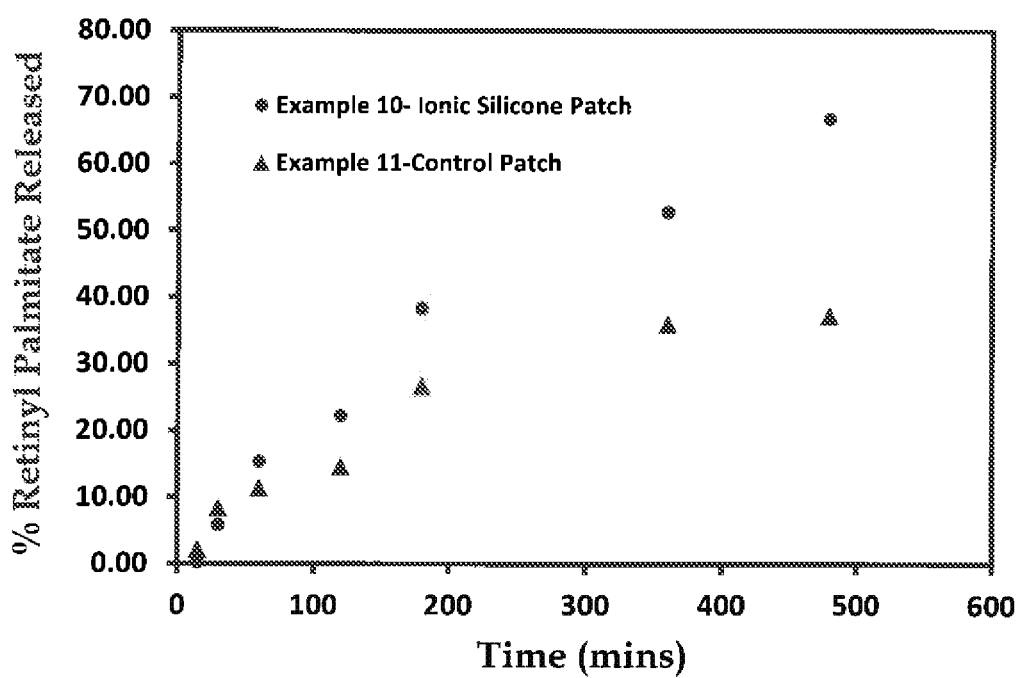

COSMETIC SKIN COVERING SHEETS AND THEIR METHOD OF PREPARATION

FIELD OF THE INVENTION

The present invention relates to skin covering, specifically skin covering sheets containing crosslinked silicone polymers that have the benefits of compatibility with hydrophilic components and solid particulates in personal care compositions and the resultant personal care applications.

BACKGROUND OF THE INVENTION

The personal care industry thrives on being able to deliver multiple performance products based on mixtures of several components, with each having performance characteristics important to or desirable in the final formulation. One desirable characteristic is the ability to provide a silky initial feel in the formulation.

Silicone copolymer gels are known in the personal care industry for many uses including their use in skin care applications. However these gels often fail to provide the desired degree of wash-off resistance, pigment dispersibility and anti-whitening properties.

In addition, such silicone copolymer gels have typically been made by methods of generating crosslinked siloxane polymers that limit the range of desirable organofunctional groups that may be incorporated into the polymeric structure to create additional performance advantages in complex formulations.

SUMMARY OF THE INVENTION

The invention is directed to a cosmetic skin covering sheet which contains an ionically-modified silicone.

In one embodiment herein there is provided a cosmetic skin covering sheet which comprises a patch containing a cosmetic material for application to the skin, or a cosmetic formulation which forms the cosmetic skin covering sheet in-situ upon topical application of the cosmetic formulation onto the skin, and wherein the cosmetic skin covering sheet contains an ionic silicone.

BRIEF DESCRIPTION OF THE DRAWING

FIG. 1 provides a graph showing the % release of retinyl palmitate from the control & example-10 ionic silicone patches.

DETAILED DESCRIPTION OF THE INVENTION

The inventors herein have unexpectedly discovered a skin covering sheet which contains an ionic silicone. The skin covering sheet can provide for good sensory benefits to the skin, e.g., a silky feel, while also providing the desired degree of cosmetic and/or dermatological benefit, pigment dispersibility and anti-whitening properties.

Other than in the working examples or where otherwise indicated, all numbers expressing amounts of materials, reaction conditions, time durations, quantified properties of materials, and so forth, stated in the specification and claims are to be understood as being modified in all instances by the term "about" whether or not the term "about" is used in the expression.

It will be understood that any numerical range recited herein includes all sub-ranges within that range and any combination of the various endpoints of such ranges or sub-ranges, be it described in the examples or anywhere else in the specification.

It will also be understood herein that any of the components of the invention herein as they are described by any specific genus or species detailed in the examples section of the specification, can be used in one embodiment to define an alternative respective definition of any endpoint of a range elsewhere described in the specification with regard to that component, and can thus, in one non-limiting embodiment, be used to supplant such a range endpoint, elsewhere described.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

In describing the products of the instant invention as a reaction product of initial materials reference is made to the initial species recited and it is to be noted that additional materials may be added to the initial mixture of synthetic precursors. These additional materials may be reactive or non-reactive. The defining characteristic of the instant invention is that the reaction product is obtained from the reaction of at least the components listed as disclosed.

Non-reactive components may be added to the reaction mixture as diluents or to impart additional properties unrelated to the properties of the composition prepared as a reaction product. Thus for example particulate solids such as pigments may be dispersed into the reaction mixture, before during or after reaction to produce a reaction product composition that additionally comprises the non-reactive component, e.g. a pigment. Additional reactive components may also be added; such components may react with the initial reactants or they may react with the reaction product; the phrase "reaction product" is intended to include those possibilities as well as including the addition of non-reactive components.

The term "active agents" used here and in the claims is defined as cosmetics that are known in the art which can be used alone or in combination in the compositions of the proposed formulations.

The term "other additives" used here and in the claims is defined as ingredients such as stabilizers, solubilizers, anti-irritants, anti-oxidants and plasticizers, anti-microbials and preservatives which can improve the efficacy and the mechanical properties of the formulation.

The term "topical application" used here and in the claims is defined as a formulation which is in contact with the outermost layer of the skin.

The term "pad" or "patch" used here interchangeably and in the claims is defined as a device that includes a backing layer, a vehicle containing the active agents and other additives and a release liner where the backing layer is located on one side of the vehicle and the release liner is located in the other side of the vehicle, and the pad may be fixed to the skin following removal of the release liner.

The expressions "cosmetic skin pad" or "cosmetic skin patch" used here and in the claims are defined as a pad that is applied to the external part of the human body (epidermis, face, neck, and hand) for changing the appearance by protecting or keeping the skin in good condition.

In one embodiment herein, the ionic silicone employed in the cosmetic skin covering sheet can comprise an ionic silicone composite network which comprises at least one ionically modified silicone with the general formula:

$$M^1_a M^2_b M^3_c D^1_d D^2_e D^3_f T^1_g T^2_h T^3_i Q_j \qquad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ where $R^1$, $R^2$, $R^3$, $R^5$, $R^6$, $R^8$, $R^9$, $R^{10}$, $R^{11}$, $R^{13}$, $R^{15}$, $R^{16}$ are aliphatic, aromatic or fluoro-containing monovalent hydrocarbon radicals containing from 1 to about 60 carbon atoms, specifically from 1 to about 20 carbon atoms and more specifically from 1 to about 8 carbon atoms, and in some embodiments, the aforestated ranges can have lower limits of 2 or 3 carbon atoms;

where $R^4$, $R^{12}$, $R^{17}$ are monovalent or multivalent radical bearing ionic group(s);

where $R^7$, $R^{14}$ and $R^{18}$ are independently selected from hydrogen, $-OR^{20}$ or unsaturated monovalent hydrocarbon radicals wherein the unsaturated monovalent hydrocarbon radicals contain from 2 to about 60 carbon atoms, more specifically from 2 to about 20 carbon atoms, and most specifically from 2 to about 8 carbon atoms, and wherein each $R^{20}$ is independently selected from hydrogen and monovalent hydrocarbon radicals of from 1 to about 60 carbon atoms, more specifically from 1 to about 20 carbon atoms, and most specifically from 1 to about 8 carbon atoms, and in some embodiments, the aforestated ranges can have lower limits of 2 or 3 carbon atoms;

where the subscripts a, b, c, d, e, f, g, h, i, j are zero or positive subject to the following limitations: the sum a+b+c+d+e+f+g+h+i+j is greater than or equal to 2 and less than or equal to 6000, specifically a+b+c+d+e+f+g+h+i+j is greater than or equal to 2 and less than or equal to 4000, more specifically a+b+c+d+e+f+g+h+i+j is less than or equal to 2000, and in some embodiments, the aforestated ranges can have lower limits of any one of 3, 4, 5, 10, 12, 18, 20, 30 and 50 as well as 100, 200, 300 and 500, b+e+h is greater than 0, more specifically b+e+h is greater than 1, even more specifically b+e+h is greater than 2, and yet even more specifically b+e+h is from 1 to about 100, further more specifically from 1 to about 50 and most specifically from 1 to about 10, wherein the stated ranges for b+e+h can in some embodiments have lower endpoints of any one of 2, 3, 4, 5, 10, 50 or 100.

In a more specific embodiment, the ionically-modified cross-linked silicone network comprising the ionically modified silicone of formula (I), is such that the monovalent ionic radicals $R^4$, $R^{12}$, $R^{17}$ are selected from the formula (II):

$$-A-I^{x-}M_n^{y+}; \qquad (II)$$

where A is a spacing group having selected from a divalent hydrocarbon and hydrocarbonoxy group each containing from 1 to about 60 carbon atoms, more specifically from 1 to about 20 carbon atoms, and most specifically from 1 to about 8 carbon atoms, and in some embodiments, the aforestated ranges can have lower limits of 2 or 3 carbon atoms, wherein the hydrocarbonoxy group contains at least one oxygen heteroatom, where superscripts x and y are positive integers, such as where x and y are independently from 1 to 6, more specifically from 1 to about 3 subject to the proviso that x is a product of n and y, and each subscript n independently has a value of from 1 to 6, more specifically from about 1 to about 3 where I is an ionic group such as sulfonate $-SO_3^-$, sulfate $-OSO_3^-$, carboxylate $-COO^-$, phosphonate $-PO_3^{2-}$ and phosphate $-OPO_3^{2-}$ group, more specifically sulfonate $-SO_3^-$, where M is hydrogen or a cation independently selected from alkali metals, alkaline earth metals, rare earth metals, transition metals, metals, metal complexes, quaternary ammonium, polymeric cations and phosphonium groups.

In one specific embodiment herein, A is a divalent arylene group selected from the group consisting of:
$-(CH_2)_l C_6 H_4 (CH_2)_k-$,
$-CH_2 CH(CH_3)(CH_2)_k C_6 H_4-$ and,
$-CH_2 CH(R^{13*})(CH_2)_l C_6 H_3 R''-$ where $R^{13*}$ is a monovalent hydrocarbon radical having from one to sixty carbon atoms, more specifically, from one to 30 carbon atoms, even more specifically from 1 to 12 carbon atoms and most specifically from 1 to 6 carbon atoms;

where l has a value of 0 to 20, more specifically from 1 to 10 and k has a value of 0 to 20, specifically from 0 to 10.

In another specific embodiment herein, A is a divalent alkylene group of the formula $-(CHR^{14*})_m-$ where m has a value of from 1 to 20, specifically from 1 to about 10 and $R^{14*}$ is hydrogen or a monovalent hydrocarbon radical having from one to sixty carbon atoms, more specifically, from one to 30 carbon atoms, even more specifically from 1 to 12 carbon atoms and most specifically from 1 to 6 carbon atoms.

In yet another specific embodiment herein, A is selected from the group consisting of —$CH_2CH_2CH_2$—, —$CH_2CH(CH_3)$—, —$CH_2CH(CH_3)CH_2$—, and —$CH_2CH_2CH(CH_2CH_3)CH_2CH_2CH_2$—.

In yet even another specific embodiment herein A is of the formula:

$$-(CHR^{20})_m-O-(CH(R^{20}(CH_2)-O)_{m'}-X-$$

wherein m has a value of from 2 to 50, more specifically from 2 to about 10 and m' has a value of from 1 to 50, more specifically from 1 to about 25 and $R^{20}$ is hydrogen or a monovalent hydrocarbon radical having from one to sixty carbon atoms, more specifically, from one to 30 carbon atoms, even more specifically from 1 to 12 carbon atoms and most specifically from 1 to 6 carbon atoms and X is null or a divalent hydrocarbon radical optionally containing at least one heteroatom, such as the non-limiting examples of O, N, S or halogen.

In one embodiment herein, M can be a cation independently selected from univalent and polyvalent forms of Li, Na, K, Cs, Mg, Ca, Ba, Zn, Cu, Fe, Ni, Ga, Al, Mn, Cr, Ag, Au, Pt, Pd, Pb, Sb, Ru, Sn and Rh, such as the non-limiting examples of $Mn^{+2}$ and $Mn^{+3}$.

In one non-limiting embodiment herein M can specifically be a cation selected from univalent and polyvalent forms of Na, K, Mg, Ca, Zn, Cu, Fe, Ni, Co and Al.

In another more specific embodiment, the ionically-modified cross-linked silicone network comprising the ionically modified silicone of formula (I), wherein the monovalent radicals $R^4$, $R^{12}$, $R^{17}$ are selected from zwitterions having the formula (III):

$$-R'-NR''_2{}^+-R'''-I \quad \quad (III)$$

where R' is a divalent hydrocarbon radical containing from 1 to about 60 carbon atoms, specifically from 1 to about 20 carbon atoms, and more specifically from 1 to about 8 carbon atoms and in some embodiments, the aforestated ranges can have lower limits of 2 or 3 carbon atoms, where R" is monovalent hydrocarbon radical containing from 1 to about 60 carbon atoms, specifically from 1 to about 20 carbon atoms and more specifically from 1 to about 8 carbon atoms, and optionally, one or more of a sulfur atom, a nitrogen atom, oxygen atom, and in some embodiments, the aforestated ranges can have lower limits of 2 or 3 carbon atoms,
where R''' is divalent hydrocarbon radical containing from 2 to about 20 carbon atoms, specifically from 2 to about 8 carbon atoms and more specifically from 2 to about 4 carbon atoms; and, I is an ionic group such as sulfonate —$SO_3^-$, sulfate —$OSO_3^-$; carboxylate —$COO^-$, phosphonate —$PO_3^{2-}$ group and phosphate —$OPO_3^{2-}$ group.

As used herein the terminology "hydrocarbon radical" includes acyclic hydrocarbon radicals, alicyclic hydrocarbon radicals and aromatic hydrocarbon radicals.

As used herein in reference to a hydrocarbon radical, the term "monovalent" means that the radical is capable of forming one covalent bond per radical, the term "divalent" means that the radical is capable of forming two covalent bonds per radical and the term "trivalent" means that the radical is capable of forming three covalent bonds per radical. Generally, a monovalent radical can be represented as having been derived from a saturated hydrocarbon compound by conceptual removal of one hydrogen atom from the compound, a divalent radical can be represented as having been derived from a saturated hydrocarbon compound by conceptual removal of two hydrogen atoms from the compound and a trivalent radical can be represented as having been derived from a saturated hydrocarbon compound by conceptual removal of three hydrogen atoms from the compound. For example, an ethyl radical, that is, a —$CH_2CH_3$ radical, is a monovalent radical; a dimethylene radical, that is, a —$(CH_2)_2$— radical, is a divalent radical and an ethanetriyl radical, that is,

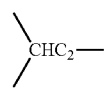

radical, is a trivalent radical, each of which can be represented as having been derived by conceptual removal of one or more hydrogen atoms from the saturated hydrocarbon ethane.

As used herein, the terminology "acyclic hydrocarbon radical" means a straight chain or branched hydrocarbon radical, preferably containing from 1 to 60 carbon atoms per radical, which may be saturated or unsaturated and which may be optionally substituted or interrupted with one or more atoms or functional groups, such as, for example, carboxyl, cyano, hydroxy, halo and oxy. As long as these functional groups do not interfere with the cationic cure mechanism of the epoxide or oxirane moiety, suitable monovalent acyclic hydrocarbon radicals may include, for example, alkyl, alkenyl, alkynyl, hydroxyalkyl, cyanoalkyl, carboxyalkyl, alkyloxy, oxaalkyl, alkylcarbonyloxaalkylene, carboxamide and haloalkyl, such as, for example, methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

Suitable divalent acyclic hydrocarbon radicals include, for example, linear or branched alkylene radicals, such as, for example, methylene, dimethylene, trimethylene, decamethylene, ethylethylene, 2-methyltrimethylene, 2,2-dimethyltrimethylene and linear or branched oxalkylene radicals such as, for example, methyleneoxypropylene.

Suitable trivalent acyclic hydrocarbon radicals include, for example, alkanetriyl radicals, such as, for example, 1,1,2-ethanetriyl, 1,2,4-butanetriyl, 1,2,8-octanetriyl, 1,2,4-cyclohexanetriyl and oxaalkanetriyl radicals such as, for example, 1,2,6-triyl-4-oxahexane.

As used herein the term "alkyl" means a saturated straight or branched monovalent hydrocarbon radical. In a preferred embodiment, monovalent alkyl groups are selected from linear or branched alkyl groups containing from 1 to 60 carbons per group, such as, for example, methyl, ethyl, propyl, iso-propyl, n-butyl, iso-butyl, sec-butyl, tert-butyl, pentyl, hexyl, heptyl, decyl, dodecyl.

As used herein the term "alkenyl" means a straight or branched monovalent terminally unsaturated hydrocarbon radical, preferably containing from 2 to 10 carbon atoms per radical, such as, for example, ethenyl, 2-propenyl, 3-butenyl, 5-hexenyl, 7-octenyl and ethenylphenyl.

As used herein, the terminology "alicyclic hydrocarbon radical" means a radical containing one or more saturated hydrocarbon rings, specifically containing from 4 to 12 carbon atoms per ring, per radical which may optionally be substituted on one or more of the rings with one or more alkyl radicals, each preferably containing from 2 to 6 carbon atoms per alkyl radical, halo radicals or other functional groups and which, in the case of a monovalent alicyclic hydrocarbon radical containing two or more rings, may be fused rings. Suitable monovalent alicyclic hydrocarbon radicals include, for example, cyclohexyl and cyclooctyl. Suitable divalent hydrocarbon radicals include, saturated or unsaturated divalent monocyclic hydrocarbon radicals, such as, for example, 1,4-cyclohexylene. Suitable trivalent alicyclic hydrocarbon radicals include, for example, cycloalkanetriyl radicals such as, for example, 1-dimethylene-2,4-cyclohexylene, 1-methylethylene-3-methyl-3,4-cyclohexylene.

As used herein, the terminology "aromatic hydrocarbon radical" means a hydrocarbon radical containing one or more aromatic rings per radical, which may, optionally, be substituted on the aromatic rings with one or more alkyl radicals, each preferably containing from 2 to 6 carbon atoms per alkyl radical, halo radicals or other functional groups and which, in the case of a monovalent aromatic hydrocarbon radical containing two or more rings, may be fused rings. Suitable monovalent aromatic hydrocarbon radicals include, for example, phenyl, tolyl, 2,4,6-trimethylphenyl, 1,2-isopropylmethylphenyl, 1-pentalenyl, naphthyl, anthryl, eugenol and allylphenol as well as aralkyl radicals such as, for example, 2-phenylethyl. Suitable divalent aromatic hydrocarbon radicals include, for example, divalent monocyclic arenes such as, for example, 1,2-phenylene, 1,4-phenylene, 4-methyl-1,2-phenylene, phenylmethylene. Suitable trivalent aromatic hydrocarbon radicals include, for example, trivalent monocyclic arenes such as, for example, 1-trimethylene-3,5-phenylene.

In one non-limiting embodiment herein, $R^1$, $R^2$, $R^3$, $R^5$, $R^6$, $R^8$, $R^9$, $R^{10}$, $R^{11}$, $R^{13}$, $R^{15}$ and $R^{16}$ are independently as described herein, and optionally wherein each can contain at least one heteroatom selected from the group consisting of oxygen and halogen.

Some specific non-limiting examples of hydrocarbon radicals that may be used herein, such as in the non-limiting example of the hydrocarbon radicals used for $R^1$, $R^2$, $R^3$, $R^5$, $R^6$, $R^8$, $R^9$, $R^{10}$, $R^{11}$, $R^{13}$, $R^{15}$ and $R^{16}$ that may be suitable are methyl, ethyl, n-propyl, iso-propyl, n-butyl, isobutyl, tert-butyl, n-pentyl, iso-pentyl, neopentyl and tert-pentyl; hexyl, such as the n-hexyl group; heptyl, such as the n-heptyl group; octyl, such as the n-octyl and isooctyl groups and the 2,2,4-trimethylpentyl group; nonyl, such as the n-nonyl group; decyl, such as the n-decyl group; cycloalkyl radicals, such as cyclopentyl, cyclohexyl, cycloheptyl radicals and methylcyclohexyl radicals. Some specific non-limiting examples of aryl hydrocarbon radicals that may be suitable are phenyl, napthyl; o-, m- and p-tolyl, xylyl, ethylphenyl and benzyl.

In one embodiment herein, the amount of ionic silicone that can be used in any one of the cosmetic skin covering sheet, the patch, the cosmetic material and/or the cosmetic formulation described herein can be in an amount of from about 99 wt % to about 0.1 wt %, more specifically from about 99 wt % to about 0.5 wt % and most specifically from about 75 wt % to about 1 wt % based on the total weight of the cosmetic skin covering sheet, the patch, the cosmetic material and/or the cosmetic formulation described herein.

In one non-limiting embodiment herein, the cosmetic covering sheet described herein can further comprise one or more of a solvent, a cosmetically acceptable additive and an excipient.

In one non-limiting embodiment herein, the solvent can be the ionic silicone described herein.

In one non-limiting embodiment herein the solvent is an ionically-modified silicone polymer having the general structure (VI):

$$M^7{}_\alpha M^8{}_\beta D^7{}_\chi D^8{}_\delta T^7{}_\epsilon T^8{}_\phi Q_\gamma. \qquad (VI)$$

wherein:
$M^7 = R^1 R^2 R^3 SiO_{1/2}$
$M^8 = R^4 R^5 R'SiO_{1/2}$
$D^7 = R^6 R^7 SiO_{2/2}$
$D^8 = R^8 R'SiO_{2/2}$
$T^7 = R^9 SiO_{3/2}$
$T^8 = R'SiO_{3/2}$
$Q = SiO_{4/2}$, and wherein, the radicals $R^1$, $R^2$, $R^3$, $R^4$, $R^5$, $R^6$, $R^7$, $R^8$ and $R^9$ are independently selected from aliphatic or aromatic monovalent hydrocarbon radicals having from 1 to 60 carbon atoms, more specifically from 1 to 30 carbon atoms, even more specifically from 1 to 12 carbon atoms and most specifically from 1 to 8 carbon atoms, and optionally each containing at least one hetero atom, such as O, N, S and halogen, and in some embodiments, the aforestated ranges can have lower limits of 2 or 3 carbon atoms and the subscripts $\alpha$, $\beta$, $\chi$, $\delta$, $\epsilon$, $\phi$, and $\gamma$ are zero or positive subject to the following limitations: $2 \leq \alpha+\beta+\chi+\delta+\epsilon+\phi+\gamma \leq 6000$, more specifically $2 \leq \alpha+\beta+\chi+\delta+\epsilon+\phi+\gamma \leq 4000$, and most specifically $2 \leq \alpha+\beta+\chi+\delta+\epsilon+\phi+\gamma \leq 2000$ and the aforestated ranges can have lower limits of any one of 3, 4, 5, 10, 12, 18, 20, 30 and 50 as well as 100, 200, 300 and 500; and, $\beta+\delta+\phi>0$, more specifically, $\beta+\delta+\phi$ is from 1 to about 100 and more specifically, $\beta+\delta+\phi$ is from 1 to about 50 and most specifically $\beta+\delta+\phi$ is from 1 to about 25, wherein said ranges of $\beta+\delta+\phi$ can have in some embodiments, upper limits of any one of 2, 3, 4, 5, 10, 50 or 100.

In another embodiment herein, solvents which are suitable for use are those compounds or mixtures of two or more compounds that are in a liquid state at or near room temperature, e.g., 20° C. to about 50° C. and about one atmosphere pressure, and include such non-limiting examples as those selected from silicone fluids, hydrocarbon fluids, esters, alcohols, fatty alcohols, glycols, organic waxes and organic oils.

In one embodiment herein the solvent can comprise a blend of two or more solvents.

In yet another embodiment, the silicone fluids may be selected from the group consisting of low viscosity silicone fluids and volatile silicone fluids.

In yet even another embodiment herein, the solvent is at least one selected from the group consisting of isodecane, isohexadecane, hydrogenated polyisobutene, jojoba, cylcopentasiloxane, dimethicone, bis-phenylpropyl dimethicone, octyldodecyl neopentanoate, oleyl oleate, oleyl alcohol and isomyristyl alcohol.

In another embodiment the carrier solvent is a cyclic silicone fluid of the general formula $D_r$, where $D=R^{15}R^{16}SiO_{2/2}$ and where $R^{15}$ and $R^{16}$ are monovalent hydrocarbon radicals of from 1 to 6 carbon atoms, more specifically methyl, and r is an integer of from 3 to 12, more specifically, from 4 to 8. Specifically, the cyclic silicone fluid can be selected from hexamethylcyclotrisiloxane, octamethylcyclotetrasiloxane, decamethylcyclopentasiloxane and dodecamethylcyclohexasiloxane.

In one embodiment, the solvent of the present invention can comprise an emollient compound. Suitable emollient compound include any fluid that provides emollient properties, that is, that when applied to skin, tend to remain on the surface of the skin or in the stratum corneum layer of the skin to act as lubricants, reduce flaking and to improve the appearance of the skin. Emollient compound are generically known and include, for example, hydrocarbons, such as for example, isododecane, isohexadecane and hydrogenated polyisobutene, organic waxes, such as for example, jojoba, silicone fluids, such as, for example, cyclopentasiloxane, dimethicone and bis-phenylpropyl dimethicone, esters, such as, for example, octyldodecyl neopentanoate and oleyl oleate, as well as fatty acids and alcohols, such as for example, oleyl alcohol and isomyristyl alcohol.

In one non-limiting embodiment herein the ionically-modified silicone crosspolymer is swellable by the solvent.

In another embodiment herein the solvent is a hydrophilic emollient selected from the group consisting of glycerine, sorbitol, aqueous solution of moisturizing additives and combinations thereof.

In one specific embodiment the solvent is selected from a silicone oil, an organic oil and combinations thereof.

Because it is possible to vary the compositional parameters of the ionically-modified silicone cross-polymer composition of the invention in an almost limitless fashion, by varying the compositional parameters of the ionically-modified silicone cross-polymer, some compositions herein are both water swellable and oil swellable while others are only water swellable or oil swellable. The amount of crosslinking present in the ionically-modified silicone cross-polymer may be characterized with respect to the degree of swelling exhibited by the cross-polymer in the solvent. In another embodiment, the crosslinked structure of the ionically-modified silicone cross-polymer is effective to allow the ionically-modified silicone cross-polymer to be swollen from its original volume to a swollen volume that is a factor of from 1.01 to 5000, more preferably from 2 to 1000, and even more preferably from 5 to 500, times its original volume. The original volume of the ionically-modified silicone cross-polymer can be determined, for example, by extracting or evaporating all of the solvent component from the personal care composition of the present invention to leave the original volume, that is, the volume of the ionically-modified silicone cross-polymer in the absence of the fluid.

In a more specific embodiment, the personal care composition (e.g. skin covering sheet (e.g. patch or cosmetic formulation)) of the present invention comprises, per 100 parts by weight ("pbw") of the ionically-modified silicone cross-polymer, from 1 pbw to 99.9 pbw, more preferably from 70 pbw to 99.5 pbw, and still more preferably from 85 pbw to 99 pbw of the solvent.

The cosmetically acceptable additive and excipients can be any of the skin benefit agents and/or cosmetic ingredients described herein. In addition, the cosmetically acceptable additives and excipients as well as the skin benefits agents or cosmetic ingredients can also comprise active ingredients selected from the group consisting of photoprotective agents, self-tanning agents, desquamating agents, depigmenting agents, moisturizing agents, skin lightening agents, anti-ageing ingredients, anti-wrinkle agents and combinations thereof.

It will be understood herein that the cosmetic material can comprise any of the cosmetically acceptable additive and excipients, the skin benefit agents and/or cosmetic ingredients or the personal care components or ingredients described herein as well as any other known cosmetic component or cosmetic active ingredient known to those skilled in the art.

In one embodiment herein the cosmetic skin covering sheet described herein contains from 0.01% to 25% by weight of the cosmetic material or active ingredient, preferably from about 0.1% to about 10% weight percent, said weight percents being based on the total weight of the sheet.

It will be understood herein that any of the embodiments described herein can be revised accordingly such that the ionically-modified cross-linked silicone network (i.e., of formula (I)), by combinations of reactants (with the solvent not being a reactant but physically entrained within the reaction product of ionically-modified cross-linked silicone network composition) using any known crosslinking means. In one non-limiting embodiment, the silicone ionomer is of the general formula (I) described herein and is produced by a reaction selected from a condensation reaction, a hydrosilylation reaction, a free-radical polymerization reaction, a ring-opening polymerization reaction and combinations thereof.

In one embodiment, the reaction is conducted as a neat reaction or in the presence of at least one cosmetic ingredient, cosmetic material or cosmetic active ingredient described herein or known to those skilled in the art.

In another embodiment, the ionic silicone composite network further comprises a physical blend of the silicone ionomer of formula (I) and an organic structuring polymer and/or another network, e.g., a silicone network other than that described herein of the present invention.

In yet another embodiment herein, the hydrosilylation reaction described herein can comprise any of the following:
ionic silyl-hydride silicone with non-ionic olefinic compound (silicone or non-silicone) and non-ionic solvent;
non-ionic silyl-hydride silicone with ionic olefinic compound (silicone or non-silicone) and non-ionic solvent;
ionic silyl-hydride silicone with ionic olefinic compound (silicone or non-silicone) and non-ionic solvent;
non-ionic silyl-hydride silicone with non-ionic olefinic compound (silicone or non-silicone) and ionic solvent;
ionic silyl-hydride silicone with non-ionic olefinic compound (silicone or non-silicone) and ionic solvent;
non-ionic silyl-hydride silicone with ionic olefinic compound (silicone or non-silicone) and ionic solvent;
ionic silyl-hydride silicone with ionic olefinic compound (silicone or non-silicone) and ionic solvent;
ionic functional, silyl-hydride functional and silyl-olefin functional compound with non-ionic solvent; and, ionic functional, silyl-hydride functional and silyl-olefin functional compound with ionic solvent.

In one non-limiting embodiment herein the crosslinked ionic silicone network can be in the absence of polyether moieties and/or polyether crosslinks. More specifically, the crosslinked ionic silicone network can be in the absence of one or more moieties selected from glycolide, lactide, butyrolactide and caprolactide. In yet a further non-limiting embodiment herein, the crosslinked ionic silicone network can be in the absence of acrylate and/or olefinic functionality. In yet a further non-limiting embodiment, the crosslinked ionic silicone network is in the absence of olefinic and hydride crosslinking.

It will be understood herein that at rest, the crosslinked ionic silicone network gel exhibits the properties of a solid gel material. The gel of the present invention exhibits high stability and resistance to syneresis, that is, the composition exhibits little or no tendency for fluid to flow from the composition and imparts high stability and syneresis resistance to personal care compositions which include the gel as a component in the oil phase. The high stability and syneresis resistance persists with prolonged aging of such personal care compositions and personal care applications containing such compositions. However, fluid may be released from the network by subjecting the silicone composition to a shearing force, such as, for example, by rubbing the composition between one's fingers, to provide improved sensory feel characteristic of the fluid component of the personal care composition.

In one other embodiment herein there is provided a skin covering sheet comprising a personal care composition containing an oil phase and an aqueous phase which personal care composition is made by the process of adding at least one crosslinked ionic silicone network gel to the oil phase of the personal care composition and wherein the crosslinked ionic silicone network gel is formed by:
a) providing a composition which comprises:
  i. at least one silicone hydride bearing at least two Si—H residues,
  ii. at least one olefin with two or more Si-unsaturated radicals,
  iii. an effective amount of precious metal catalyst suitable for facilitating addition cure reaction between (a) and b, and
  iv. optionally, a solvent suitable for swelling the said cross-polymer;
subject to the limitation that at least one of (i), (ii) or (iv) is selected from an ionically modified silicone of general formula (I):

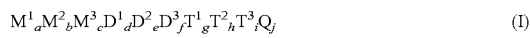  (I)

as described herein; and,
b) reacting the composition of step (a) to provide for an ionically-modified crosslinked silicone network; and,
c) and, shearing the crosslinked ionic silicone network during and/or after the reacting step with at least solvent (iv) to form the crosslinked ionic silicone network gel.

In one embodiment herein, the at least one silicone hydride bearing at least two Si—H residues and the silicon hydride activator described below that is used herein is such that it is suitable for either a crosslinking hydrosilylation reaction and/or a ring opening of the oxirane moiety of the oxirane silicone copolymer bearing ionic radicals in order to provide for the crosslinking present in the resultant crosslinked ionic silicone network. It can include any silicon compound derived from at least two organosiloxane units and having terminal and/or pendant Si—H groups. In one embodiment herein the at least one silicone hydride bearing at least two Si—H residues or the silicon-hydride activator is such that it contains at least some Si—H functional units along its polymer backbone. It may or may not in addition to these internal Si—H functional units also contain terminal Si—H functional units.

In one embodiment the at least one silicone hydride bearing at least two Si—H residues or the silicone hydride activator (the Si—H functional silicon compound-as a group comprising both embodiments) in the olefin-hydride reaction is capable of reacting with the olefinic moieties of the above-mentioned oxirane moieties via addition reaction. Examples of suitable Si—H functional silicon compounds include 1,1,3,3-tetraalkyldisiloxane, dialkylhydrogensiloxy-endstopped polydialkylsiloxane, polydialkylalkylhydrogensiloxane copolymer, and trialkylsiloxy-endstopped polydialkyl-alkylhydrogensiloxane copolymer comprising at least two alkylhydrogen siloxy groups. Other examples of Si—H containing silicon compounds include 1,1,3,3-tetramethyldisiloxane, 2,4,6,8-tetramethylcyclotetrasiloxane, methyldimethoxysilane, triethylsilane, and methyldiethoxysilane. The preferred silicon hydride activator used in the present invention is 1,1,3,3-tetramethyldisiloxane.

Although the Si—H functional silicon compound may be a silane, it is most advantageous to use an Si—H functional polysiloxane linear polymer. Thus, one embodiment of the present invention utilizes an Si—H functional linear polysiloxane polymer represented by the formula:

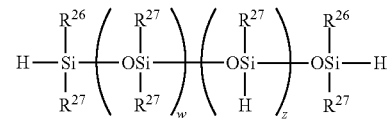

wherein $R^{26}$ and $R^{27}$ are each independently a monovalent hydrocarbon radical of from 1 to about 60 carbon atoms, specifically from 1 to about 20 carbon atoms and more specifically from 1 to about 8 carbon atoms, and in some embodiment, the aforestated ranges can have lower limits of 2 or 3 carbon atoms;
"w" is from 1 to about 1,000; and "z" is from about 5 to about 200. More preferably, "w" varies from about 10 to about 500 and "z" varies from about 5 to about 200.

Another embodiment of the present invention utilizes cyclic silicone hydrides as the Si—H functional silicon compound. Such cyclic silicone hydrides are well known in the art and may be represented by the formula:

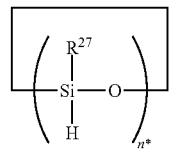

wherein $R^{27}$ is as defined above and "n*" is from about 3 to about 12, specifically from about 4 to about 10.

In one non-limiting embodiment, the amount of the Si—H functional silicon compound present in the cosmetic skin covering sheet is from about 0.01 pbw to about 10 pbw, more specifically from about 0.05 pbw to about 7 pbw and most specifically from about 0.1 pbw to about 5 pbw based on 100 parts by weight of the olefinic component or the oxirane silicone copolymer bearing ionic radicals.

In one embodiment herein the at least one olefin or silyl-olefin group containing silicone which contains at least two silyl-olefin groups is selected from the group consisting of at least one of non-silicone olefin and organo-modified silicone olefin, wherein the organo-modified silicone olefin has the general structure (V) as described herein.

In another more specific embodiment, the at least one olefin can comprise a combination of a non-silicone olefin such as the non-limiting example of an am-diene, and an organo-modified silicone olefin of the general structure (V) as described herein:

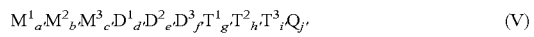  (V)

In one embodiment herein, some non-limiting examples of α,ω-diene include butadiene, hexadiene, octadiene, norbornene, ethylidene norbornene, vinylnorbornene, norbornadiene, and dicyclopentadiene and combinations thereof.

In yet another more specific embodiment, the at least one olefin comprises a blend of at least one multifunctional olefin and a mono-functional olefin.

In another more specific embodiment herein $R^O$ is a monovalent olefin radical having the structure (VII):

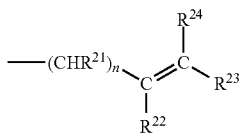

(VII)

where $R^{21}$, $R^{22}$, $R^{23}$ and $R^{24}$ are each independently selected from the group of hydrogen and monovalent hydrocarbon radicals containing from 1 to 60 carbon atoms, more specifically 1 to 30 carbon atoms, even more specifically from 1 to 12 carbon atoms and most specifically from 1 to about 6 carbon atoms.

In one embodiment, the amounts of hydride-functional silicone (i) and olefin (ii) that is employed in the process(es) described herein can be present in any amount that provides for a molar equivalent amount of silicon-hydride moieties to the molar amount of unsaturated moieties present in the olefin (ii). In one non-limiting embodiment, either the molar amount of silicon-hydride moieties present in the hydride-functional silicone (i) exceed the molar amount of unsaturated moieties present in the olefin (ii) or vice-versa, the molar amount of unsaturated moieties present in the olefin (ii) exceed the molar amount of silicon-hydride moieties present in the hydride-functional silicone (i). In a more specific embodiment the amount of hydride-functional silicone (i) that is employed in the process(es) described herein can be present in any equivalent amount that provides for a molar ratio of silicon-hydride moieties in silicone (i) to unsaturated moieties in olefin (ii) of from 1:100 to about 100:1, more specifically from about 1:10 to about 10:1.

In one embodiment herein the solvent (iv) can be any of the solvent described herein.

In one embodiment herein, the amount of solvent (iv) that can be employed in the process(es) and compositions described herein comprise from about 0 weight percent to about 99.9 weight percent, more specifically from about 0 weight percent to about 99 weight percent and most specifically from about 0 weight percent to about 95 weight percent, said weight percents being based on the total weight of the ionically-modified silicone cross-polymer composition for the skin covering sheet. In one embodiment herein the lower endpoint of the aforementioned ranges can be any one of 0.1 weight percent, 0.5 weight percent, 1 weight percent, 5 weight percent and 10 weight percent.

Many types of previous metal catalysts, e.g., platinum catalysts are known and such platinum catalysts may be used for the hydrosilylation reaction in the present invention. When optical clarity is required the preferred platinum catalysts are those platinum compound catalysts that are soluble in the reaction mixture. The platinum compound can be selected from those having the formula ($PtCl_2$Olefin) and H($PtCl_3$Olefin) as described in U.S. Pat. No. 3,159,601, hereby incorporated by reference. A further platinum containing material usable in the compositions of the present invention is the cyclopropane complex of platinum chloride described in U.S. Pat. No. 3,159,662 hereby incorporated by reference. Further the platinum containing material can be a complex formed from chloroplatinic acid with up to 2 moles per gram of platinum of a member selected from the class consisting of alcohols, ethers, aldehydes and mixtures of the above as described in U.S. Pat. No. 3,220,972 hereby incorporated by reference. The catalysts most specifically used herein are described in U.S. Pat. Nos. 3,715,334; 3,775,452; and 3,814,730 to Karstedt. Additional background concerning the art may be found at J. L. Spier, "Homogeneous Catalysis of Hydrosilation by Transition Metals, in Advances in Organometallic Chemistry, volume 17, pages 407 through 447, F. G. A. Stone and R. West editors, published by the Academic Press (New York, 1979).

In one embodiment the precious metal catalysts that may be used herein, are such as the non-limiting examples of rhodium, ruthenium, palladium, osmium, iridium and platinum catalysts and combinations thereof.

In one embodiment herein the platinum catalyst is in a soluble complex form.

In one other embodiment, the platinum catalyst is selected from the group consisting of platinic chloride, chloroplatinic acid, bis(acetylacetonato)platinum, ($\eta^5$-Cyclopentadienyl)trialkylplatinum and combinations thereof.

Persons skilled in the art can easily determine an effective amount of precious metal catalyst. The catalyst can be present in a very wide range, but normally a range of from between 0.1 and 10,000 ppm, more specifically from between 1 and 100 ppm. In one embodiment herein the basis amount of the catalyst is based on the amount of ionically-modified silicone cross-polymer or the amounts of the respective components used to produce the ionically-modified silicone cross-polymer.

In one specific embodiment herein the steps (b) and (c) of the process(es) described herein can be conducted at a temperature of from about 0° C. to about 200° C., more specifically, from about 10° C. to about 150° C. and most specifically from about from about 20° C. to about 120° C., and at a pressure of from about 0.1 atm to about 10 atm, more specifically of from about 0.5 atm to about 5 atm and most specifically of from about 0.9 atm to about 2 atm.

In one specific embodiment herein the steps (b) and (c) of the process(es) described herein (either separately or together) can be conducted for a period of from about 5 minutes to about 48 hours, more specifically from about 20 minutes to about 36 hours and most specifically from about 1 hour to about 12 hours.

In one embodiment the process of preparing an ionically-modified silicone cross-polymer composition for personal care applications can further comprise the use of a hydrosilylation inhibitor, such as the non-limiting example of mercaptyl compounds. In one embodiment the inhibitor can be used during step (b) of the process of preparing an ionically-modified silicone cross-polymer composition for personal care applications. Non-limiting examples of hydrosilylation inhibitors are described in U.S. Pat. Nos. 3,445,420, 4,256,870, 4,465,818, 4,562,096, and 5,629,387, the disclosures of which are hereby incorporated by reference. It is well within the skill in the art to select a suitable hydrosilylation inhibitor.

It will be understood herein that the respective R values, subscripts and other variables defined herein can have the same definitions in the process embodiments herein as these variables have in the composition embodiments described herein and vice-versa.

In one embodiment herein that the reaction of hydride-functional silicone (i) with olefin (ii) can be conducted under general hydrosilylation conditions which can comprises the use of an effective amount of precious metal catalyst (iii) such as those catalysts described herein, e.g., a platinum catalyst, and in the presence of a solvent (iv) and in conditions as described herein and/or as are known to those skilled in the art.

In one embodiment herein, it is to be noted that acetylene analogs of the olefin (ii) will react to form similar products. Thus, as used herein, the phrase an "olefin selected from non-silicones and organo-modified silicones with the general structure (V)", is intended to also include an acetylenically unsaturated molecule. The phrase "an acetylenically unsaturated molecule" means a molecule possessing one or more interior, pendant or terminal carbon carbon triple bonds, i.e. a —C≡C— linkage.

The ionic silicon hydride (i) and vinyl (ii) functionalities can be made by a variety of techniques that are known in the art, such as those described in U.S. Pat. No. 8,697,829, the contents of which are incorporated by reference herein.

The non-ionic silicone olefins (ii) can be made by a variety of techniques that are known in the art. They are typically prepared by equilibration reactions of suitable monomers catalyzed by acids or bases.

The solvent (iv) when it is of the general formula (VI) can be made by a variety of techniques that are known in the art, such as those described in JP 6,247,827 and JP 6,247,835, the contents of which are incorporated by reference herein.

In one other embodiment herein there is provided a skin covering sheet comprising a personal care composition containing an oil phase and an aqueous phase which personal care composition is made by the process of adding at least one crosslinked ionic silicone network gel to the oil phase of the personal care composition and wherein the crosslinked ionic silicone network gel is formed by polymerizing
i) at least one oxirane-functionalized compound;
ii) an oxirane ring-opening polymerization catalyst;
iii) a solvent; and,
iv) optionally, one or more silicon hydride activators,
wherein at least one of (i), (iii) or (iv) comprises a silicone of formula (I) as described herein
and wherein the crosslinked ionic silicone network is formed by the ring-opening polymerization of oxirane moiety with hydride moiety; and,
shearing the crosslinked ionic silicone network during and/or after the polymerization step with at least carrier solvent (iii) to form the crosslinked ionic silicone network gel.
In one embodiment herein the oxirane ring-opening polymerization catalyst is an acid catalyst capable of polymerizing an epoxy group.

In a more specific embodiment, the acid catalyst capable of polymerizing an epoxy group is selected from onium salt generated acids; metal salts selected from the group consisting of aluminum trichloride and ferric chloride; lanthanide triflates; and, platinum compounds.

In one even more specific embodiment, the acid catalyst is a lanthium triflate of the general formula:

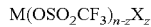

where M is the cation derived from a lanthanide and n is the valence of the lanthanide in the compound, X is an additional organic or inorganic salt residue (anionic residue), z is a number lower than n or 0.

The term "lanthanide" (M) shall be selected out of lanthanum and each of the chemical elements whose atomic number is between 58 (cerium) and 71 (lutetium), inclusive. In one specific embodiment, the lanthanide is selected from the group consisting of lanthan, ytterbium and samarium.

Some lanthanide triflates are commercial products or can be obtained by conventional, well-known methods. As X other organic and/or inorganic salt residues can be used, e.g., anions such as $Cl^-$, $Br^-$, $I^-$, $NO_3^-$, $HSO_4^-$, $H_2PO_3^-$, $HCO_3^-$, $CH_3COO^-$, $C_2H_5OO^-$, $C_6H_5COO^-$ which may form mixed salts with the lanthanide M.

Z is a number between 0 and n−1, so that at least one triflate residue is included in the lanthium triflate. More specifically the lanthium triflate is such that Z is 0 or 1, more specifically Z is 0. The lanthium triflate may comprise one or more metal ions M which may be the same or different.

In another embodiment herein the oxirane ring-opening polymerization-effective catalyst can be a platinum catalyst which operates under cationic cure conditions to ring-open the oxirane group of the oxirane silicone copolymer bearing ionic radicals. It will be understood herein that cationic polymerization conditions comprise any reaction parameters that provide for the ring-opening of the oxirane moiety with a silyl-hydride moiety.

Cationic polymerization conditions can be generated by addition of an acid catalyst capable of polymerizing an epoxy group such as, for example, by addition of onium salt generated acids and certain metal salts, such as, for example, aluminum trichloride and ferric chloride, which act as Lewis acids or by addition of lanthanide triflates, see PCT int. Appl. WO 0008,087. Acid catalyzed polymerization of epoxides is a well known method of forming organic polymers and has been applied to epoxy-functional siloxane compounds in order to form siloxane polyalkyleneoxide block copolymers for use in a variety of applications as, for example, release coatings on paper, see, for example, U.S. Pat. No. 4,279,717, and in conjunction with organic materials to form coatings and modified plastic compositions, see for example, U.S. Pat. Nos. 5,354,796 and 5,663,752.

One precautionary note must be observed, that is if the cationic polymerization is conducted in the presence of cyclic siloxanes, e.g. $D_3$, $D_4$ or $D_5$ and the like, the strength of the acid catalysis employed must be such that cationic polymerization of the epoxide moiety occurs but polymerization of the cyclic siloxane does not occur to any appreciable extent.

In one embodiment the oxirane ring-opening polymerization catalyst can be any of the precious metal catalysts described herein.

In one other embodiment, the solvent can be any of the solvents described herein.

In yet a further embodiment the silicon hydride activator can be any of the Si—H containing compounds described herein.

In one embodiment herein the cosmetic skin covering sheet can comprise a cosmetic patch containing a cosmetic material for application to the skin. Further, the cosmetic patch containing a cosmetic material may comprise more than one layer, wherein at least one of the layers comprises the ionic silicone as described herein, e.g., the ionic silicone network of formula (I).

The content of cosmetic ingredient in the cosmetic patch may be appropriately determined according to the type and purpose of use, but in too small an amount the effectiveness will be reduced. No particular problem results if the cosmetic ingredient is in a supersaturated state or in a precipitated crystal state. Cosmetic ingredients may also be encapsulated together with absorption accelerators, or a retaining layer may be provided for the cosmetic ingredients.

In another embodiment herein the patch can comprise more than one layer, e.g., more than one substrate layer, and wherein at least one layer comprises the ionic silicone composite network containing the ionically modified silicone of the general formula (I).

A cosmetic patch of the invention may be produced by a pressure-sensitive adhesive tape production process known in the prior art. In a solution coating method, for example, prescribed amounts of a plasticizer, cosmetic ingredient, and the like are mixed with a solution containing the ionic silicone described herein, if necessary with dilution using an organic solvent, and the obtained solution is used for coating and drying onto a support (backing layer), or is coated and dried on a release sheet (release layer) and then transferred to a support.

Flexible substrates that may be used herein as the support, may either be woven or non-woven. The hydrophilic fibers of the substrate may be natural materials such as cellulosics selected from the group consisting of wood pulp, cotton, hemp, jute, flax and fiber mixtures thereof. Semi-synthetic and synthetic hydrophilic fibers such as rayon and hydrophilic polyesters may also be employed. The most preferred fiber is rayon. Hydrophobic fibers normally are synthetic plastics of sufficiently high molecular weight to melt above about 20° C., preferably above 50° C., selected from the group consisting of polyvinyl acetate, polyacrylic, polymethacrylic, polyamide, styrene copolymers, hydrophobic polyester, polyolefin, polyurethane, polyvinylchloride, inorganics and combinations thereof. Examples of these include acrylonitrile-based acrylics, nylons (e.g. nylon 6, nylon 66, nylon 610), polyethylene terephthalate, polypropylene and polyethylene.

Preferably substrate fiber diameters may range from about 0.1 to about 50 µm, but higher or lower sizes may be suitable depending on fiber type and binder systems.

The term "hydrophilic" is used to describe materials which are wetted by water (i.e. the surfaces of the materials have contact angles with water less than 90°. By contrast, the term "hydrophobic" is used to describe materials which are not wetted by water (i.e. the surfaces of hydrophobic materials have contact angles with water greater than 90°). While it is relatively straight forward to determine contact angle directed by optical measurements at the liquid-solid interface between water and flat solid surfaces, it is relatively complex to obtain contact angle between individual fibers or filaments in water. Yet these measurements may be accomplished utilizing a Wilhelmy balance principal. Relative hydrophilic/hydrophobic nature of individual fibers or filaments can be calculated through the fiber wettability values.

Fiber material which ordinarily has been classified as hydrophobic or hydrophilic may be treated with a surface coating to alter its water philicity properties. Hydrophilic properties may be imparted by coating with a surfactant. These materials may include alkyl ether sulfates, alkyl benzene sulfonates, fatty acid soaps, polyalkoxylated derivatives of sorbitan, of $C_6$-$C_{20}$ alcohols or of $C_6$-$C_{20}$ fatty acids, polyglycerol fatty acid esters and combinations thereof. Alternatively, hydrophilic properties may be applied to a hydrophobic fiber core by treatment of the latter with a coating of a silicone oil (high molecular weight dimethicone) or a fluorine containing substance.

Generally, non-woven substrates are those prepared by air-laying or water-laying processes in which the fibers or filaments are first cut to the desired length from long strands, passed into water or airstreams, and then deposited onto a screen or mesh through which the fiber-laid in air or water is passed. The resulting non-woven layer, regardless of its method or production or composition, is then subjected to at least one of several types of bonding operations to anchor the individual fibers together to form a self-sustaining web. One non-limiting process for preparing the non-woven substrate includes thermal bonding.

Optionally, the non-woven substrate may be treated with a suitable polymeric resin or binder in order to fortify the bonding of the fibers. Examples of such resins or binders include those comprising monomers selected from the group consisting of styrene monomers, derivatized styrene monomers, butadiene monomers, derivatized butadiene monomers and mixtures thereof.

In one embodiment, a hydrogel adhesive is deposited on a major surface of the flexible substrate, optionally in conjunction with the ionic silicone as described herein. In one embodiment herein the hydrogel adhesive may comprise the ionic silicone described herein. Hydrogels are defined as coherent, three-dimensional aqueous polymer systems capable of absorbing water without liquefying. Generally the amount of water within the hydrogel may range from about 20 to about 95%, preferably from about 30 to about 90%, more preferably from about 45 to about 85%, optimally from at least 50 to 80% by weight. Illustrative of hydrogel adhesives are gelatins, polysaccharides, polyacrylamides, polyacrylates, polyvinylpyrrolidone, polyalkylene oxides, mixtures of the aforementioned polymers and mixtures of monomers forming the aforementioned polymers into copolymers. These polymers may be crosslinked (graft or free-radical induced) or non-crosslinked. Specific polymers include polyacrylamide, polyhydroxyethylmethacrylate, poly(2-acrylamido-2-methylpropanesulfonic acid), polyacrylic acid, polyvinylpyrrolidone, polyvinylalcohol and mixtures thereof. Most preferred are polyacrylics.

In one non-limiting embodiment, the cosmetic skin covering sheet may be formed of a hydrophilic fibrous nonwoven fabric or a finely porous plastic film. The cosmetic skin covering sheet support or other layer in the cosmetic skin covering sheet may be formed of either of a hydrophobic fibrous nonwoven fabric, a breathable but liquid-impervious plastic film, two-layers of a nonwoven fabric laminated with a hydrophobic fibrous nonwoven fabric, and a composite sheet consisting of a hydrophobic fibrous nonwoven fabric and a breathable but liquid-impervious plastic film bonded to this hydrophobic fibrous nonwoven fabric.

It is also possible to form the cosmetic skin covering sheet using a composite nonwoven fabric with a highly water-resistant fibrous nonwoven fabric made by melt-blown process sandwiched by two layers of spun bonded fibrous nonwoven fabric having high strength and flexibility.

Nonwoven fabric used herein may be selected from a group of nonwoven fabrics manufactured by such a process as spun lacing-, needle punching-, melt blowing-, thermal bonding-, spun bonding-, chemical bonding- and air through-processes. Component fiber of such a nonwoven fabric may be selected from a group of materials including polyolefin-, polyester- and polyamide-based fibers and core-sheath type or side-by-side type conjugated fibers of polyethylene/polypropylene or polyethylene/polyester.

The cosmetic skin covering sheet may be formed with any one of the materials including stretchable hydrophobic fibrous nonwoven fabric, stretchable and breathable but liquid-impervious plastic film, two layers of stretchable hydrophobic fibrous nonwoven fabric laminated with each other, and composite sheet consisting stretchable hydrophobic fibrous nonwoven fabric and stretchable, breathable but liquid-impervious plastic film laminated with each other.

The stretchable fibrous nonwoven fabric may be any one of melt-blown nonwoven fabric and spun bonded nonwoven fabric. As the component fiber of the stretchable nonwoven fabric, stretchable fiber obtained by melt-spinning a thermoplastic elastomer resin can be used. Alternatively, a composite nonwoven fabric consisting of first hydrophobic fibrous nonwoven fabric of thermoplastic elastomer resin fiber and second hydrophobic fibrous nonwoven fabric of a crimped fiber obtained by melt-spinning a thermoplastic synthetic resin selected from a group of polypropylene, polyethylene and polyester wherein the second hydrophobic fibrous nonwoven fabric is bonded to at least one surface of the first hydrophobic fibrous nonwoven fabric.

As examples of cosmetic ingredients to be contained in cosmetic skin covering sheet there may be mentioned whitening ingredients such as ascorbyl palmitate, kojic acid, lucinol, and oil-soluble licorice extract, wrinkle preventers such as retinol, retinoic acid, retinol acetate and retinol palmitate, circulation improving ingredients such as vitamin E, tocopherol acetate, capsaicin and vanillylamide nonylate, antimicrobial ingredients such as isopropylmethylphenol, light-sensitive elements and zinc oxide, and vitamins such as vitamin $D_2$, vitamin $D_3$ and vitamin K.

The content of cosmetic ingredient in the skin patch may be appropriately determined according to the type and purpose of use, but in too small an amount the effectiveness will be reduced while in too large an amount the adhesive property of the patch will be reduced, and therefore they are preferably added at 0.01-50 wt % in the skin patch. No particular problem results if the cosmetic ingredient is in a supersaturated state or in a precipitated crystal state in the cosmetic skin covering sheet. Cosmetic ingredients may also be encapsulated together with absorption accelerators, or a retaining layer may be provided for the cosmetic ingredients.

A cosmetic patch obtained using a pressure-sensitive adhesive for skin according to the invention may also contain added absorption accelerators, dissolution aids or preventers, aromatic agents, and the like. The thickness of the pressure-sensitive adhesive layer for skin of the invention is not particularly restricted. However, if it is too thin the cosmetic ingredient content must be increased and the adhesion will be reduced. If it is too thick, the cosmetic ingredient in the pressure-sensitive adhesive near the support will not readily diffuse to the pressure-sensitive adhesive layer surface, thereby lowering the cosmetic release property. In most cases, the thickness is preferably 10-200 µm.

In an embodiment of the invention, the cosmetic pad may be applied to a selected area of skin for a predetermined time ranging from 0.5 to 24 hours, preferably up to 8 hours and more preferably 4 hours per day. An intensive course of treatment may require at least a 3 month course of application for achieving a significant improvement in skin appearance.

The hydrogel adhesive and flexible substrate may be present in relative weight ratios of from about 50:1 to about 1:50, preferably from about 10:1 to about 1:10, optimally from about 2:1 to about 1:2 by weight.

The skin patch of the present invention may be of any size or geometry. The skin patch may be round, oval, or semicircular, among others. The patch may also be of full-face dimensions with cut-out areas for the eyes, nose and/or mouth.

Skin patches of the present invention ordinarily will also include a backing layer (support layer) across the hydrogel adhesive on a side opposite to that of the substrate. Ordinarily the backing layer will be hydrophobic or if hydrophilic will be coated with a hydrophobic coating for quick release from the adhesive. Plastic films are particularly suitable including polyethylene, polyester, polyurethane, polyvinyl chloride, polyamide and metallic foils. The backing film can be a composite or a single layer material. Physically it may appear transparent, opaque, fleshtoned or aluminized.

Skin conditioners, moisturizers and surfactants may be included as additives within the hydrogel adhesive. Illustrative conditioners include mineral oil, petrolatum, vegetable oils (such as soybean or maleated soybean oil), dimethicone, dimethicone copolyol, cationic monomers and polymers (such as distearyl dimethyl ammonium chloride). Illustrative moisturizers are polyols such as sorbitol, glycerin, propylene glycol, ethylene glycol, polyethylene glycol, polypropylene glycol, 1,3-butane diol, hexylene glycol, isoprene glycol, xylitol, fructose and mixtures thereof.

Surfactants may be those selected from the anionic, cationic, nonionic, amphoteric, zwitterionic and combinations thereof. Most preferred are nonionic and amphoteric surfactants due to their mildness.

Amounts of the conditioners, moisturizers and surfactants may each independently range from about 0.01 to about 45%, preferably from about 0.1 to about 30%, optimally from about 1 to about 20% by weight for each category.

Skin benefit agents other than cosmetic ingredients described above may also be included in the skin patches of the present invention. These further additives may be selected from retinoids (e.g. retinol and retinyl linoleate), ascorbic acid and derivatives thereof, herbal extracts and combinations thereof. Amounts of these materials may range anywhere from 0.0001 to 5% by weight.

In preferred embodiments of the present invention, cosmetic active agents known in the art may be incorporated in the polymeric matrix of the skin patch for improving skin appearance. These agents can be any of anti-blotching, anti-aging, eye contour, slimming, soothing/sunburn, anti-irritating, skin firming and lifting, free radical scavengers, hydratives, vitamins and anti-oxidants and minerals.

In one other embodiment herein the cosmetic skin covering sheet can comprise a cosmetic formulation which forms the cosmetic skin covering sheet in-situ upon topical application of the cosmetic formulation onto the skin in conjunction with the ionic silicone described herein.

The expression "forms the cosmetic skin covering sheet in-situ" is understood to mean that the application of the cosmetic formulation to the skin is a liquid, cream or spreadable solid cosmetic face mask material that can be spread, dabbed, applied, painted or coated onto the skin in any manner known for applying cosmetic face masks and optionally, followed by the drying or evaporation of any volatile materials in the face mask material, at which point the face mask material can optionally be continued to be worn for a period as described herein following, at which time it can then be rubbed off, washed off or peeled off, or removed by other known methods, otherwise the cosmetic material may be removed immediately after application. The face mask material may be worn on the face for a period that will attribute the dermatological or cosmetic benefit desired from the cosmetic material, and can include any known benefit resulting from the use of any of the cosmetic materials described herein.

As examples of cosmetic ingredients to be contained in the cosmetic formulation for the skin covering sheets formed in situ include those described above for skin patches.

The cosmetic delivery sheets produced in situ could be used anywhere on the face or body skin to predetermined areas for delivery of ingredients. The exact size and shape of the cosmetic sheet formed in situ will depend upon the intended use and product characteristics. The cosmetic sheet formed in situ will have sufficient flexibility, and a size and shape adapted to conform to the desired treatment area of the user's skin. In a particularly preferred, but not necessary, embodiment of the present invention, the cosmetic sheet formed in situ is a facial mask adapted to conform to facial features. It will be understood that a variety of shapes and sizes may be accommodated according to the invention. Such a cosmetic sheet formed in situ may include a flexible substrate that is formed of, preferably but not necessarily, water-soluble or non-water soluble materials, such as sugar or polysaccharides, collagen, and water-soluble film-forming polymers. The substrate contains multiple isolate, discrete regions, while at least two of such regions are imprinted with different skin benefit agents for treating different skin conditions.

Suitable skin benefit agents can be used in the present invention include, but are not limited to: anti-wrinkle or skin-tightening agents; anti-aging agents; moisturizing agents; skin-whitening or depigmentation agents; anti-inflammatory agents; anti-acne agents; stretch-mark/scar removing agents; dark circle reduction agents; and, antioxidants.

The cosmetic delivery sheets produced in situ may also comprise a gel, such as a hydrogel, comprised of, for example, agarose or a water-soluble low-substituted cellulose ether which may include methyl cellulose, hydroxyethyl cellulose, hydroxypropyl cellulose, hydroxypropylmethyl cellulose, hydroxypropylhydroxyethyl cellulose, hydroxyethylmethyl cellulose, ethyl cellulose, hydroxyethylethyl cellulose, or carboxymethyl cellulose. In a preferred but not necessary embodiment of the present invention, the skin benefit agents of the cosmetic sheet formed in situ are completely water-soluble, such as sugar, so upon application of water or like liquid activator, the cosmetic sheet formed in situ softens and conforms to the skin, and subsequently, the entire sheet is absorbed by the skin surface without having to be removed.

The skin care compositions that may be present in the cosmetic sheet formed in situ according to the invention are, in particular, W/O or O/W skin creams, day and night creams, eye creams, face creams, antiwrinkle creams, moisturizing creams, bleaching creams, vitamin creams, skin lotions, care lotions and moisturizing lotions.

It is understood herein that the various descriptive support provided in the respective embodiments described herein applies equally and interchangeably to all portions and embodiments of the specification. Thus, it is understood herein that the respective R definitions, subscript values and other variables defined herein with regard to one embodiment, can have the same definitions with regard to the description section in another embodiment, as well as the process embodiments herein, and also in any other way these variables have been described elsewhere in the composition or process embodiments described herein, and vice-versa.

It will be understood herein that any reference to personal care compositions, emulsions, applications and ingredients are in regard to their presence as components of a cosmetic skin covering sheet as described herein.

In one embodiment herein, the compositions of the present invention are self-emulsifying.

In another embodiment herein, the personal care composition in the cosmetic skin covering sheet described herein may be further processed under low to high shear to adjust the viscosity and sensory feel of the composition. This may be achieved, for example, by subjecting the composition to a moderate to high shearing force. High shear may be applied using, for example, a Sonolator apparatus, a Gaulin Homogenizer or a Micro Fluidizer apparatus. Optionally, one or more carrier solvent may be added to the silicone composition prior to the shearing.

In a specific embodiment, the personal care composition in the skin covering sheet of the present invention is a solid, typically having a creamy consistency, wherein the ionically-modified silicone cross-polymer acts as a means for gelling the fluid to reversibly impart characteristics of a solid to the fluid. At rest, the personal care composition in the skin covering sheet exhibits the properties of a solid gel material. The personal care composition of the present invention exhibits high stability and resistance to syneresis, that is, the composition exhibits little or no tendency for fluid to flow from the composition and imparts high stability and syneresis resistance to personal care compositions which include the ionically-modified silicone cross-polymer as a component. The high stability and syneresis resistance persists with prolonged aging of such ionically-modified silicone cross-polymer and personal care compositions. However, solvent may be released from the ionically-modified silicone cross-polymer by subjecting the personal care composition to a shearing force, such as, for example, by rubbing the composition between one's fingers, to provide improved sensory feel characteristic of the fluid component of the silicone material.

Water (or a water equivalent such as a non-aqueous hydroxylic solvent), siloxane, linear or cyclic, or lipophilic fluid (oil swelling agent, oil swellable) may be used as the solvent which may function as a swelling agent. Lipophilic fluids suitable for use as the solvent component of the composition of the present invention are those described herein. In a preferred embodiment, the solvent component of the composition of the present invention exhibits a viscosity of below about 1,000 cSt, preferably below about 500 cSt, more preferably below about 250 cSt, and most preferably below 100 cSt, at 25° C.

In one preferred embodiment, the cross-polymer is an ionically-modified silicone cross-polymer that is insoluble in various fluid components, but that is capable of being swollen by the solvent. The amount of crosslinking present in the ionically-modified silicone cross-polymer may be characterized with respect to the degree of swelling exhibited by the cross-polymer in the solvent.

In another specific embodiment, the cross linked structure of the ionically-modified silicone cross-polymer is effective to allow the cross-polymer to be swollen by a low molecular weight silicone fluid, such as, for example, decamethylcyclopentasiloxane, from its original volume to a swollen volume as stated above.

The ionically-modified silicone cross-polymer of the present invention may be utilized as prepared or as the silicone component in personal care emulsions for use in the cosmetic skin covering sheet. As is generally known, emulsions comprise at least two immiscible phases one of which is continuous and the other which is discontinuous. In one embodiment herein, the non-miscible phases (immiscible phases) can be selected from the group consisting of aqueous, non-aqueous, and solid particulates.

Further emulsions may be liquids with varying viscosities or solids. Additionally, the particle size of the emulsions may render them microemulsions, and when sufficiently small, microemulsions may be transparent. Further it is also possible to prepare emulsions of emulsions and these are generally known as multiple emulsions. These emulsions may be: 1) aqueous emulsions where the discontinuous phase comprises water and the continuous phase comprises the cross linked ionic silicone network of the present invention; 2) aqueous emulsions where the discontinuous phase comprises the ionically-modified silicone cross-polymer of the present invention and the continuous phase comprises water; 3) non-aqueous emulsions where the discontinuous phase comprises a non-aqueous hydroxylic solvent and the continuous phase comprises the conically-modified silicone cross-polymer of the present invention; and 4) non-aqueous emulsions where the continuous phase comprises a non-aqueous hydroxylic organic solvent and the discontinuous phase comprises the ionically-modified silicone cross-polymer of the present invention.

In one embodiment herein, the ionically-modified silicone cross-polymer is compatible with a particulate additive. In another more specific embodiment, the particulate additive is selected from inorganic particulates, polymeric latexes, and pigments.

As used herein the term "non-aqueous hydroxylic organic compound" or "non-aqueous hydroxylic solvent" means hydroxyl containing organic compounds exemplified by alcohols, glycols, polyhydric alcohols and polymeric glycols and mixtures thereof that are liquid at room temperature, e.g. about 25° C., and about one atmosphere pressure, and are used interchangeably with the term "solvent" as the same component. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, isopropyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a high viscosity cream with good feel characteristics, and high absorbance of volatile siloxanes. It is capable of being blended into personal care formulations for hair care, skin care, and the like. In one embodiment herein, the crosslinked ionic silicone network can bind and slow release cosmetic actives.

In one embodiment the cosmetic skin covering sheet described herein can contain further personal care application components selected from the group consisting of deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nail creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a more specific embodiment, the personal care application components of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with ionically-modified silicone cross-polymer composition.

Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions; such as is described above.

In one useful embodiment, an antiperspirant composition comprises the ionically-modified silicone cross-polymer composition of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

In another useful embodiment, a skin care composition comprises the ionically-modified silicone cross-polymer, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoyl methane, p-aminobenzoic acid and octyl dimethyl-p-aminobenzoic acid.

In another useful embodiment, a color cosmetic composition, such as, for example, a lipstick, a makeup or a mascara composition comprises the crosslinked ionic silicone network, and a coloring agent, such as a pigment, a water soluble dye or a liposoluble dye.

In another useful embodiment, the compositions of the present invention are utilized in conjunction with fragrant materials. These fragrant materials may be fragrant compounds, encapsulated fragrant compounds or fragrance releasing compounds that either the neat compounds or are encapsulated.

It will be understood herein that the ionically-modified silicone cross-polymer composition for personal care applications, such as the ionically-modified silicone cross-polymer composition made by the process(es) described herein, can be such that there are no polyether crosslinks in the ionically-modified silicone cross-polymer.

EXAMPLES a. Ionic Silicone Gel Patches

Example 1

Varying amounts of vinyl end capped polydimethyl-co-methyl-2-methylpropylphenylsulfonate siloxane with 0.062 mmol·g−1 vinyl and 0.328 mmol·g−1 sulfonate was mixed with vinyl end capped polydimethylsiloxane with 0.3 mmol·g−1 vinyl, vinyl end capped polydimethylsiloxane with 0.13 mmol·g−1 vinyl, Vinyl end capped polydimethyl siloxane with 1.08 mmol·g−1 vinyl, vinyl end capped polydimethylsiloxane with 0.03 mmol·g−1 vinyl, hydride functional polydimethylsiloxane with 1.4 mmol·g−1 silicon-hydride, hydride terminated polydimethylsiloxane chain extender with 1.4 mmol·g−1 silicon-hydride, and chain inhibitor 1,3-divinyldimethylsiloxane (MviMvi) and blended in a high speed mixer for 3 minutes at 2200 rpm. Platinum catalyst was added to the above mixture and again blended in a speed mixer for 30 seconds at 2000 rpm. Resulting mixture was quickly poured onto a skin-mimicking membrane with 450 nm pore size or drawn as a thin film on a PET sheet followed by curing at room temperature. Upon curing a soft, tacky composition was obtained.

TABLE 1

Addition cure adhesive gel patches containing vinyl functional sulfonated PDMS

| Component (functional group mmol · g−1) | Example 1 (wt %) |
|---|---|
| Vinyl terminated PDMS (0.3) | 20.99 |
| Vinyl terminated PDMS (0.13) | 9.8 |
| Vinyl terminated PDMS (0.03) | 9.8 |
| Vinyl terminated sulfonated PDMS (0.062) | 50.50 |
| Vinyl Terminated PDMS (1.08) | 0.99 |
| Hydride functional PDMS (1.4) | 0.99 |
| Hydride Terminated PDMS (1.4) | 6.78 |
| MviMvi (10.72) | 0.01 |
| Pt-D | 0.14 |

Example 2

Adhesive Gel Patches Containing Niacinamide

Varying amounts of vinyl end capped polydimethyl-co-methyl-2-methylpropylphenylsulfonate siloxane with 0.062 mmol·g−1 vinyl and 0.328 mmol·g−1 sulfonate was mixed with vinyl end capped polydimethylsiloxane with 0.3 mmol·g−1 vinyl, vinyl end capped polydimethylsiloxane with 0.13 mmol·g−1 vinyl, Vinyl end capped polydimethyl siloxane with 1.08 mmol·g−1 vinyl, vinyl end capped polydimethylsiloxane with 0.03 mmol·g−1 vinyl, hydride functional polydimethylsiloxane with 1.4 mmol·g−1 silicon-hydride, hydride terminated polydimethylsiloxane chain extender with 1.4 mmol·g−1 silicon-hydride, and chain inhibitor 1,3-divinyldimethylsiloxane (MviMvi), and Niacinamide stock solution (stock solution prepared by dissolving 0.21 g Niacinamide in 1.79 g glycerin) and blended in a high speed mixer for 3 minutes at 2200 rpm. Platinum catalyst was added to the above mixture and again blended in a speed mixer for 30 seconds at 2000 rpm. Resulting mixture was quickly poured onto a skin-mimicking membrane with 450 nm pore size or drawn as a thin film on a PET sheet followed by curing at room temperature. Upon curing a soft, tacky adhesive patch containing 0.5% of niacinamide was obtained.

TABLE 2

Addition cure adhesive gel patches of vinyl functional sulfonated PDMS containing Niacinamide

| Component (functional group mmol · g−1) | Example 2 (wt %) |
|---|---|
| Vinyl terminated PDMS (0.3) | 20.00 |
| Vinyl terminated PDMS (0.13) | 9.34 |
| Vinyl terminated PDMS (0.03) | 9.34 |
| Vinyl terminated sulfonated PDMS (0.062) | 48.10 |
| Vinyl Terminated PDMS (1.08) | 0.94 |
| Hydride functional PDMS (1.4) | 0.94 |
| Hydride Terminated PDMS (1.4) | 6.46 |
| MviMvi (10.72) | 0.01 |
| Pt-D | 0.13 |
| Niacinamide | 0.50 |
| Glycerin | 4.24 |

Example 3

Adhesive Gel Patches Containing Arbutin

Varying amounts of vinyl end capped polydimethyl-co-methyl-2-methylpropylphenylsulfonate siloxane with 0.062 mmol·g−1 vinyl and 0.328 mmol·g−1 sulfonate was mixed with vinyl end capped polydimethylsiloxane with 0.3 mmol·g−1 vinyl, vinyl end capped polydimethylsiloxane with 0.13 mmol·g−1 vinyl, Vinyl end capped polydimethyl siloxane with 1.08 mmol·g−1 vinyl, vinyl end capped polydimethylsiloxane with 0.03 mmol·g−1 vinyl, hydride functional polydimethylsiloxane with 1.4 mmol·g−1 silicon-hydride, hydride terminated polydimethylsiloxane chain extender with 1.4 mmol·g−1 silicon-hydride, and chain inhibitor 1,3-divinyldimethylsiloxane (MviMvi), and Arbutin stock solution (stock solution prepared by dissolving 0.04 g Arbutin in 1.6 g glycerin & 0.2 g water) and blended in a high speed mixer for 3 minutes at 2200 rpm. Platinum catalyst was added to the above mixture and again blended in a speed mixer for 30 seconds at 2000 rpm. Resulting mixture was quickly poured onto a skin-mimicking membrane with 450 nm pore size or drawn as a thin film on a PET sheet followed by curing at room temperature. Upon curing a soft, tacky adhesive patch containing 0.1% of Arbutin was obtained.

TABLE 3

Addition cure adhesive gel patches of vinyl functional sulfonated PDMS containing Arbutin

| Component (functional group mmol · g−1) | Example 3 (wt %) |
|---|---|
| Vinyl terminated PDMS (0.3) | 20.08 |
| Vinyl terminated PDMS (0.13) | 9.38 |
| Vinyl terminated PDMS (0.03) | 9.38 |
| Vinyl terminated sulfonated PDMS (0.062) | 48.30 |
| Vinyl Terminated PDMS (1.08) | 0.94 |
| Hydride functional PDMS (1.4) | 0.95 |
| Hydride Terminated PDMS (1.4) | 6.49 |
| MviMvi (10.72) | 0.01 |
| Pt-D | 0.13 |

TABLE 3-continued

Addition cure adhesive gel patches of vinyl functional sulfonated PDMS containing Arbutin

| Component (functional group mmol · g−1) | Example 3 (wt %) |
|---|---|
| Arbutin | 0.1 |
| Water | 0.47 |
| Glycerin | 3.78 |

Ionic Silicone Adhesive Patches

Example 4 to Example 7

Varying amounts of vinyl end capped polydimethyl-co-methyl-2-methylpropylphenylsulfonate siloxane with 0.062 mmol·g−1 vinyl and 0.328 mmol·g−1 sulfonate was mixed with vinyl end capped polydimethylsiloxane with 0.3 mmol·g−1 vinyl, vinyl end capped polydimethylsiloxane with 0.13 mmol·g−1 vinyl, Vinyl end capped polydimethyl siloxane with 1.08 mmol·g−1 vinyl, vinyl end capped polydimethylsiloxane with 0.03 mmol·g−1 vinyl, hydride functional polydimethylsiloxane with 1.4 mmol·g−1 silicon-hydride, hydride terminated polydimethylsiloxane chain extender with 1.4 mmol·g−1 silicon-hydride, and chain inhibitor 1,3-divinyldimethylsiloxane ($M^{vi}M^{vi}$) and blended in a high speed mixer for 3 minutes at 2200 rpm. Platinum catalyst was added to the above mixture and again blended in a speed mixer for 30 seconds at 2000 rpm. Resulting mixture was poured into a Teflon coated molds followed by curing at room temperature. Upon curing a soft, tacky self-standing adhesive patch was obtained. The cross linker and chain extender content was varied to get self-standing films of varying softness and tack.

TABLE 4

Addition cure adhesive patches of vinyl functional sulfonated PDMS of varying tack

| Component (functional group mmol · g−1) | Example 4 (wt %) | Example 5 (wt %) | Example 6 (wt %) | Example 7 (wt %) |
|---|---|---|---|---|
| Vinyl terminated PDMS (0.3) | 20.22 | 20.12 | 20.08 | 20.0 |
| Vinyl terminated PDMS (0.13) | 9.44 | 9.40 | 9.40 | 9.39 |
| Vinyl terminated PDMS (0.03) | 11.90 | 12.03 | 12.23 | 12.42 |
| Vinyl terminated sulfonated PDMS (0.062) | 48.49 | 48.70 | 49.13 | 49.51 |
| Vinyl Terminated PDMS (1.08) | 0.94 | 0.98 | 1.04 | 1.10 |
| Hydride functional PDMS (1.4) | 2.27 | 2.14 | 2.01 | 1.87 |
| Hydride Terminated PDMS (1.4) | 6.31 | 5.96 | 5.60 | 5.20 |
| MviMvi (10.72) | 0.01 | 0.01 | 0.01 | 0.01 |
| Pt-D | 0.42 | 0.44 | 0.47 | 0.49 |

Example 8

Adhesive Patches Containing Niacinamide

Varying amounts of vinyl end capped polydimethyl-co-methyl-2-methylpropylphenylsulfonate siloxane with 0.062 mmol·g−1 vinyl and 0.328 mmol·g−1 sulfonate was mixed with vinyl end capped polydimethylsiloxane with 0.3 mmol·g−1 vinyl, vinyl end capped polydimethylsiloxane with 0.13 mmol·g−1 vinyl, Vinyl end capped polydimethylsiloxane with 1.08 mmol·g−1 vinyl, vinyl end capped polydimethylsiloxane with 0.03 mmol·g−1 vinyl, hydride functional polydimethylsiloxane with 1.4 mmol·g−1 silicon-hydride, hydride terminated polydimethylsiloxane chain extender with 1.4 mmol·g−1 silicon-hydride, and chain inhibitor 1,3-divinyldimethylsiloxane (MviMvi), and Niacinamide stock solution (stock solution prepared by dissolving 0.21 g Niacinamide in 1.79 g glycerin) and blended in a high speed mixer for 3 minutes at 2200 rpm. Platinum catalyst was added to the above mixture and again blended in a speed mixer for 30 seconds at 2000 rpm. Resulting mixture was poured into a Teflon coated molds followed by curing at room temperature. Upon curing a soft, tacky self-standing adhesive patch containing 0.5% Niacinamide was obtained.

TABLE 5

Addition cure adhesive patches of vinyl functional sulfonated PDMS containing Niacinamide

| Component (functional group mmol · g−1) | Example 8 (wt %) |
|---|---|
| Vinyl terminated PDMS (0.3) | 19.15 |
| Vinyl terminated PDMS (0.13) | 8.95 |
| Vinyl terminated PDMS (0.03) | 11.46 |
| Vinyl terminated sulfonated PDMS (0.062) | 46.37 |
| Vinyl Terminated PDMS (1.08) | 0.93 |
| Hydride functional PDMS (1.4) | 2.03 |
| Hydride Terminated PDMS (1.4) | 5.68 |
| MviMvi (10.72) | 0.01 |
| Pt-D | 0.42 |
| Niacinamide | 0.50 |
| Glycerin | 4.47 |

Example 9

Adhesive Patches Containing Arbutin

Varying amounts of vinyl end capped polydimethyl-co-methyl-2-methylpropylphenylsulfonate siloxane with 0.062 mmol·g−1 vinyl and 0.328 mmol·g−1 sulfonate was mixed with vinyl end capped polydimethylsiloxane with 0.3 mmol·g−1 vinyl, vinyl end capped polydimethylsiloxane with 0.13 mmol·g−1 vinyl, Vinyl end capped polydimethyl siloxane with 1.08 mmol·g−1 vinyl, vinyl end capped polydimethylsiloxane with 0.03 mmol·g−1 vinyl, hydride functional polydimethylsiloxane with 1.4 mmol·g−1 silicon-hydride, hydride terminated polydimethylsiloxane chain extender with 1.4 mmol·g−1 silicon-hydride, and chain inhibitor 1,3-divinyldimethylsiloxane (MviMvi), and Arbutin stock solution (stock solution prepared by dissolving 0.3 g Arbutin in 1.7 g glycerin & 1.0 g water) and blended in a high speed mixer for 3 minutes at 2200 rpm. Platinum catalyst was added to the above mixture and again blended in a speed mixer for 30 seconds at 2000 rpm. Resulting mixture was quickly poured onto a skin-mimicking membrane with 450 nm pore size or drawn as a thin film on a PET sheet followed by curing at room temperature. Upon curing a soft, tacky adhesive patch containing 0.5% of Arbutin was obtained.

TABLE 6

Addition cure adhesive patches of vinyl functional sulfonated PDMS containing Arbutin

| Component (functional group mmol · g−1) | Example 9 (wt %) |
|---|---|
| Vinyl terminated PDMS (0.3) | 19.15 |
| Vinyl terminated PDMS (0.13) | 8.95 |
| Vinyl terminated PDMS (0.03) | 11.46 |
| Vinyl terminated sulfonated PDMS (0.062) | 46.37 |
| Vinyl Terminated PDMS (1.08) | 0.93 |
| Hydride functional PDMS (1.4) | 2.03 |
| Hydride Terminated PDMS (1.4) | 5.68 |
| MviMvi (10.72) | 0.01 |
| Pt-D | 0.42 |
| Arbutin | 0.50 |
| Ethanol | 1.69 |
| Glycerin | 2.80 |

Example 10

Adhesive Patches Containing Retinyl Palmitate

Varying amounts of vinyl end capped polydimethyl-co-methyl-2-methylpropylphenylsulfonate siloxane with 0.062 mmol·g−1 vinyl and 0.328 mmol·g−1 sulfonate was mixed with vinyl end capped polydimethylsiloxane with 0.3 mmol·g−1 vinyl, vinyl end capped polydimethylsiloxane with 0.13 mmol·g−1 vinyl, Vinyl end capped polydimethyl siloxane with 1.08 mmol·g−1 vinyl, vinyl end capped polydimethylsiloxane with 0.03 mmol·g−1 vinyl, hydride functional polydimethylsiloxane with 1.4 mmol·g−1 silicon-hydride, hydride terminated polydimethylsiloxane chain extender with 1.4 mmol·g−1 silicon-hydride, and chain inhibitor 1,3-divinyldimethylsiloxane (MviMvi), and Retinyl Palmitate stock solution (stock solution prepared by dissolving 0.4 g Retinyl Palmitate in 1.5 g Isopropyl myristate) and blended in a high speed mixer for 3 minutes at 2200 rpm. Platinum catalyst was added to the above mixture and again blended in a speed mixer for 30 seconds at 2000 rpm. Resulting mixture was quickly poured onto a skin-mimicking Strat-M™ membrane or drawn as a thin film on a PET sheet followed by curing at room temperature. Upon curing a soft, tacky adhesive patch containing 1.82% of Retinyl Palmitate was obtained.

TABLE 7

Addition cure adhesive patches of vinyl functional sulfonated PDMS containing Retinyl Palmitate

| Component (functional group mmol · g−1) | Example 10 (wt %) |
|---|---|
| Vinyl terminated PDMS (0.3) | 18.39 |
| Vinyl terminated PDMS (0.13) | 8.58 |
| Vinyl terminated PDMS (0.03) | 10.82 |
| Vinyl terminated sulfonated PDMS (0.062) | 44.08 |
| Vinyl Terminated PDMS (1.08) | 0.85 |
| Hydride functional PDMS (1.4) | 2.06 |
| Hydride Terminated PDMS (1.4) | 5.74 |
| MviMvi (10.72) | 0.01 |
| Pt-D | 0.38 |
| Retinyl Palmitate | 1.82 |
| Isopropyl myristate | 7.27 |

Example 11

Control Adhesive Patches Containing Retinyl Palmitate

Varying amounts of vinyl end capped polydimethylsiloxane with 0.05 mmol·g−1 vinyl was mixed with vinyl end capped polydimethylsiloxane with 0.3 mmol·g−1 vinyl, vinyl end capped polydimethylsiloxane with 0.13 mmol·g−1 vinyl, Vinyl end capped polydimethyl siloxane with 1.08 mmol·g−1 vinyl, vinyl end capped polydimethylsiloxane with 0.03 mmol·g−1 vinyl, hydride functional polydimethylsiloxane with 1.4 mmol·g−1 silicon-hydride, hydride terminated polydimethylsiloxane chain extender with 1.4 mmol·g−1 silicon-hydride, and chain inhibitor 1,3-divinyldimethylsiloxane (MviMvi), and Retinyl Palmitate stock solution (stock solution prepared by dissolving 0.4 g Retinyl Palmitate in 1.5 g Isopropyl myristate) and blended in a high speed mixer for 3 minutes at 2200 rpm. Platinum catalyst was added to the above mixture and again blended in a speed mixer for 30 seconds at 2000 rpm. Resulting mixture was quickly poured onto a skin-mimicking Strat-M™ membrane or drawn as a thin film on a PET sheet followed by curing at room temperature. Upon curing a soft, tacky adhesive patch containing 1.82% of Retinyl Palmitate was obtained.

TABLE 8

Addition cure control adhesive patches of vinyl functional PDMS containing Retinyl Palmitate

| Component (functional group mmol · g−1) | Example 10 (wt %) |
|---|---|
| Vinyl terminated PDMS (0.3) | 19.69 |
| Vinyl terminated PDMS (0.13) | 8.70 |
| Vinyl terminated PDMS (0.03) | 10.72 |
| Vinyl terminated PDMS (0.05) | 42.87 |
| Vinyl Terminated PDMS (1.08) | 0.87 |
| Hydride functional PDMS (1.4) | 2.02 |
| Hydride Terminated PDMS (1.4) | 5.64 |
| MviMvi (10.72) | 0.01 |
| Pt-D | 0.39 |
| Retinyl Palmitate | 1.82 |
| Isopropyl myristate | 7.27 |

In Vitro Retinyl Palmitate Release Testing:

Typically, 300-400 mg of thoroughly mixed formulations mentioned in Example 10 (Ionic silicone patch) and Example 11 (control patch) were separately spread over a shiny side of the Strat-M™ membrane. The membrane was placed in a Franz diffusion cell in such a way that the side on which formulation was applied faces upwards while other side of the membrane is in direct contact with the receiver medium, 1-octanol. The release rate experiment was carried out at 22±1° C. Samples (~0.4 mL) were withdrawn from the receiver medium at predetermined time intervals 15, 30, 60, 120, 180, 360, & 480 mins, and the volume sampled was replaced with fresh receptor medium (1-octanol). Sink condition was achieved by selecting a receiver medium with a high capacity to dissolve the active-retinyl palmitate. Typically, the receiver medium and amount of sample applied was decided so that the active concentration does not exceed 10-20% of the active solubility in receptor medium at the end of the release test. The % retinyl palmitate release was plotted against the time. Retinyl palmitate was quantified using reversed phase HPLC (C18 column). Retinyl palmitate release was monitored with UV detector at 300 nm using Acetonitrile-Water-Isopropyl alcohol (IPA) mobile phase.

Under this method, retinyl palmitate eluted at 15.8 min. Mobile phase composition was varied as given below.

| Time min. | Water % | Acetonitrile % | IPA % |
|---|---|---|---|
| 0.01 | 70 | 20 | 10 |
| 5.00 | 70 | 20 | 10 |
| 10.00 | 0 | 80 | 20 |
| 15.00 | 0 | 10 | 90 |
| 20.00 | 0 | 10 | 90 |
| 21.00 | 70 | 20 | 10 |
| 25.00 | 70 | 20 | 10 |

TABLE 9

Table showing the % retinyl palmitate released from control & ionic silicone adhesive formulation at given time.

| Time mins | Control Patch (% Retinyl Palmitate released) | Example-10 IS patch (% Retinyl Palmitate released) |
|---|---|---|
| 15 | 2.12 | 0.18 |
| 30 | 8.41 | 5.81 |
| 60 | 11.36 | 15.30 |
| 120 | 14.57 | 22.18 |
| 180 | 26.68 | 38.30 |
| 360 | 35.90 | 52.72 |
| 480 | 37.25 | 66.71 |

% Retinyl palmitate released from control & Ionic silicone patch (Example 10) was plotted against the time at which aliquots were taken; please refer to the FIG. 1 below. It is clearly visible that significantly more retinyl pahnitate was released from ionic silicone patch than the control patch. FIG. 1 shown below provides a graph showing the % release of retinyl palmitate from the control & example-10 ionic silicone patches

Mask Formulations

Mask Formulation 1

Comparative Example

| Components | Weight (g) |
|---|---|
| Water (Deionized) | to 100 |
| Polyvinyl alcohol | 16 |
| Thickener | 0.55 |
| Glycerin | 3.0 |
| PEG 300 | 3.0 |
| Tergitol 15-S-7 | 2.0 |
| Ethanol | 5.5 |
| Perfume, Preservative, color | qs |

Mask Formulation 2

Inventive Example

| Components | Weight (g) |
|---|---|
| Water (Deionized) | -to 100 |
| Polyvinyl alcohol | 12 |
| Thickener | 0.55 |
| Magnasoft 800L (Momentive) | 4.0 |
| Glycerin | 3.0 |
| PEG 300 | 3.0 |
| Tergitol 15-S-7 | 2.0 |
| Ethanol | 5.5 |
| Perfume, Preservative, color | qs |

Mask Formulation 3

Inventive Example

| Components | Weight (g) |
|---|---|
| Water (Deionized) | -to 100 |
| Polyvinyl alcohol | 10 |
| Thickener | 0.55 |
| Magnasoft 800L (Momentive) | 6.0 |
| Glycerin | 3.0 |
| PEG 300 | 3.0 |
| Tergitol 15-S-7 | 2.0 |
| Sodium hydroxide (1% sol in water) | qs for pH 7 |
| Ethanol | 5.5 |
| Perfume, Preservative, color | qs |

The above noted examples clearly demonstrate that all of the ionic silicone based compositions have shown significant improvement over traditional non-ionic silicone based composition with respect to the compatibility with hydrophilic and lipophilic ingredients, pigment dispersion and sensory feeling.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

The invention claimed is:

1. A cosmetic skin covering sheet which comprises a patch containing a cosmetic material for application to the skin or a cosmetic formulation which forms the cosmetic skin covering sheet in-situ upon topical application of the cosmetic formulation onto the skin, and the said cosmetic skin covering sheet is produced by a reaction selected from a condensation reaction, a hydrosilylation reaction, a free-radical polymerization reaction, a ring-opening polymerization reaction and combinations thereof, wherein the reaction is conducted in the presence of
(i) at least one ionic silicone having the general formula:

$$M^1_a M^2_b M^3_c D^1_d D^2_e D^3_f T^1_g T^2_h T^3_i Q_j \tag{I}$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$ $D^1 = R^{10}R^{11}SiO_{2/2}$
$D^2 = R^{12}R^{13}SiO_{2/2}$
$D^3 = R^{14}R^{15}SiO_{2/2}$
$T^1 = R^{16}SiO_{3/2}$
$T^2 = R^{17}SiO_{3/2}$
$T^3 = R^{18}SiO_{3/2}$
$Q = SiO_{4/2}$ where $R^1, R^2, R^3, R^5, R^6, R^8, R^9, R^{10}, R^{11}, R^{13}, R^{15}, R^{16}$ are independently an aliphatic, an aromatic or fluoro containing monovalent hydrocarbon radicals containing from 1 to about 60 carbon atoms;

where $R^4, R^{12}, R^{17}$ are monovalent or multi-valent radical bearing ion-pairs, where $R^7, R^{14}$ and $R^{18}$ are independently selected from hydrogen, $—OR^{20}$ and an unsaturated monovalent radical, wherein each $R^{20}$ is independently selected from hydrogen, and a monovalent hydrocarbon radical of from 1 to about 60 carbon atoms, where the subscripts a, b, c, d, e, f, g, h, i, j are zero or positive subject to the following limitations: the sum a+b+c+d+e+f+g+h+i+j is greater than or equal to 2 and less than or equal to 6000, and b+e+h is greater than 0; and (ii) at least one compound selected from a hydrosilylation effective component, a condensation effective component, free radical polymerization effective component and a ring-opening polymerization component;

with the proviso that when $R^7, R^{14}$ and $R^{18}$ are hydrogen then the hydrosilylation effective component is selected from a vinyl silicone and hydrosilylation effective catalyst, and when $R^7, R^{14}$ and $R^{18}$ are unsaturated monovalent radicals the hydrosilylation effective component is selected from a hydride silicone and hydrosilylation effective catalyst.

2. The cosmetic skin covering sheet of claim 1 further comprising a solvent, a cosmetically acceptable additive, an excipient and combinations thereof.

3. The cosmetic skin covering sheet of claim 1, wherein the patch containing a cosmetic material for application to the skin comprises greater than one layer and wherein at least one such layer comprises the ionic silicone.

4. The cosmetic skin covering sheet of claim 1, wherein the cosmetic formulation which forms the cosmetic skin covering sheet in-situ upon topical application of the cosmetic formulation onto the skin takes the contour of the skin substrate upon application to the skin.

5. The cosmetic skin covering sheet of claim 1, wherein the sheet further comprises from 0.01% to 25% by weight of an active ingredient, based on a total weight of the sheet.

6. The cosmetic skin covering sheet of claim 1 where in the ionically modified silicone the monovalent radicals $R^4$, $R^{12}, R^{17}$ are independently selected from the formula (II):

where A is a spacing group having selected from a divalent hydrocarbon and hydrocarbonoxy group each containing from 1 to about 60 carbon atoms, wherein the hydrocarbonoxy group contains at least one oxygen heteroatom, where superscripts x and y are positive integers, subject to the proviso that x is a product of n and y, and each subscript n independently has a value of from 1 to 6, where I is an ionic group, and where M is hydrogen or a cation independently selected from alkali metals, alkaline earth metals, rare earth metals, transition metals, metals, metal complexes, quaternary ammonium, polymeric cations and phosphonium groups.

7. The cosmetic skin covering sheet of claim 1 where in the ionically modified silicone the monovalent radicals $R^4$, $R^{12}, R^{17}$ are independently selected from zwitterions having the formula (III):

where R' is a divalent hydrocarbon radical containing from 1 to about 60 carbon atoms, where R'' is monovalent hydrocarbon radical containing from 1 to about 60 carbon atoms, and optionally, one or more of a sulfur atom, a nitrogen atom, oxygen atom, where R''' is divalent hydrocarbon radical containing from 2 to about 20 carbon atoms; and, I is an ionic group.

8. The cosmetic skin covering sheet of claim 1 wherein the reaction(s) is conducted as a neat reaction or in presence of at least one of a cosmetic ingredient and an excipient.

9. The cosmetic skin covering sheet of claim 1, wherein the ionic silicone composite network further comprises a physical blend of the silicone ionomer of formula (I) and an organic structuring polymer and/or another network.

10. The cosmetic skin covering sheet of claim 9, wherein the physical blend further comprises at least one of a cosmetic ingredient, an active ingredient and an excipient.

11. The cosmetic skin covering sheet of claim 10, wherein the active ingredient is selected from the group consisting of photoprotective agents, self-tanning agents, desquamating agents, depigmenting agents, moisturizing agents, skin lightening agents, anti-aging ingredients, anti-wrinkle agents, and combinations thereof.

12. A method for providing the skin cosmetic covering sheet of claim 1 which comprises physically blending (1) the ionic silicone and (ii) at least one compound selected from a hydrosilylation effective component, a condensation effective component, free radical polymerization effective component and a ring-opening polymerization component.

13. The method of claim 12 wherein the skin cosmetic covering sheet is a patch containing a cosmetic material for application to the skin.

14. The method of claim 12, wherein the skin cosmetic covering sheet is a cosmetic formulation which forms the cosmetic skin covering sheet in-situ upon topical application of the cosmetic formulation onto the skin.

15. The method of claim 12 where in the ionically modified silicone the monovalent radicals $R^4, R^{12}, R^{17}$ are independently selected from the formula (II):

where A is a spacing group having selected from a divalent hydrocarbon and hydrocarbonoxy group each containing from 1 to about 60 carbon atoms, wherein the hydrocarbonoxy group contains at least one oxygen heteroatom, where superscripts x and y are positive integers, subject to the proviso that x is a product of n and y, and each subscript n independently has a value of from 1 to 6, where I is an ionic group, and where M is hydrogen or a cation independently selected from alkali metals, alkaline earth metals, rare earth metals, transition metals, metals, metal complexes, quaternary ammonium, polymeric cations and phosphonium groups.

16. The method of claim 12 where in the ionically modified silicone the monovalent radicals $R^4$, $R^{12}$, $R^{17}$ are independently selected from zwitterions having the formula (III):

$$—R'—NR''_2{}^+—R'''—I \qquad (III)$$

where R' is a divalent hydrocarbon radical containing from 1 to about 60 carbon atoms,
where R" is monovalent hydrocarbon radical containing from 1 to about 60 carbon atoms, and optionally, one or more of a sulfur atom, a nitrogen atom, oxygen atom,
where R''' is divalent hydrocarbon radical containing from 2 to about 20 carbon atoms; and, I is an ionic group.

17. The method of claim 12, wherein the ionic silicone is produced by a reaction selected from a condensation reaction, a hydrosilylation reaction, a free-radical polymerization reaction, a ring-opening polymerization reaction and combinations thereof.

18. The cosmetic skin covering sheet of claim 1 wherein the component (ii) is selected from silicone hydride, silicone vinyl, silanol, alkoxy silicone, alkoxy silane or silicone resins.

19. The cosmetic skin covering sheet of claim 1 wherein the hydrosilylation effective component is selected from organic molecules bearing two or more hydrosilylation effective unsaturations.

* * * * *